(12) United States Patent
Ogata et al.

(10) Patent No.: US 12,205,129 B2
(45) Date of Patent: Jan. 21, 2025

(54) INFORMATION MANAGEMENT SYSTEM, INFORMATION MANAGEMENT METHOD, AND PROGRAM

(71) Applicant: I-PEX Inc., Kyoto (JP)

(72) Inventors: Kenji Ogata, Ogori (JP); Shohei Takeda, Ogori (JP)

(73) Assignee: I-PEX Inc., Kyoto (JP)

( * ) Notice: Subject to any disclaimer, the term of this patent is extended or adjusted under 35 U.S.C. 154(b) by 0 days.

(21) Appl. No.: 17/798,274

(22) PCT Filed: Feb. 8, 2021

(86) PCT No.: PCT/JP2021/004580
§ 371 (c)(1),
(2) Date: Aug. 8, 2022

(87) PCT Pub. No.: WO2021/171987
PCT Pub. Date: Sep. 2, 2021

(65) Prior Publication Data
US 2023/0075086 A1 Mar. 9, 2023

(30) Foreign Application Priority Data
Feb. 28, 2020 (JP) .................. 2020-034043

(51) Int. Cl.
*G06Q 30/0203* (2023.01)
*G01N 33/00* (2006.01)

(52) U.S. Cl.
CPC ..... *G06Q 30/0203* (2013.01); *G01N 33/0062* (2013.01)

(58) Field of Classification Search
CPC ............... G06Q 30/0203; G06Q 30/02; G01N 33/0062; G01N 27/12; G01N 27/227;
(Continued)

(56) References Cited

U.S. PATENT DOCUMENTS

2008/0131858 A1* 6/2008 Gordon .............. G09B 19/0076
434/327
2012/0143804 A1 6/2012 Haddad et al.
(Continued)

FOREIGN PATENT DOCUMENTS

EP 3 187 852 A1 7/2017
JP 2017221640 A 12/2017
(Continued)

OTHER PUBLICATIONS

Supplementary European Search Report, Application No. EP 21 76 0590, Date of Completion of the Search May 23, 2023, The Hague.
(Continued)

*Primary Examiner* — Francis Z. Santiago Merced
(74) *Attorney, Agent, or Firm* — Howard & Howard Attorneys PLLC

(57) ABSTRACT

An information management system (1) includes an odor sensor (2) and an information processor (3). The odor sensor (2) senses an odor emitted from a source (T). The information processor (3) includes a preference information inputter (11) and a user information acquirer (12). The user information acquirer (12) acquires user information indicating the attribute of a user. The preference information inputter (11) inputs preference information indicating the preference of the user for the odor sensed by the odor sensor (2). A storage (20) associates odor information indicating the kind of the odor sensed by the odor sensor (2), the user information acquired by the user information acquirer (12), and the preference information input into the preference information inputter (11) with each other, and stores the odor information, the user information, and the preference information.

10 Claims, 19 Drawing Sheets

(58) Field of Classification Search
CPC ... G01N 33/0031; G01B 11/026; G01S 15/08; G01W 1/02; G06T 7/00; G16H 10/60
USPC ........................................................ 705/7.32
See application file for complete search history.

(56) References Cited

U.S. PATENT DOCUMENTS

| | | | |
|---|---|---|---|
| 2017/0354231 | A1 | 12/2017 | Okumura et al. |
| 2018/0036448 | A1* | 2/2018 | Becker ...................... A61L 9/04 |
| 2018/0266977 | A1 | 9/2018 | Hashizume |
| 2018/0318706 | A1* | 11/2018 | Nishimaki ............. G09F 19/00 |
| 2018/0369847 | A1 | 12/2018 | Kihm et al. |
| 2018/0373272 | A1 | 12/2018 | Kihm et al. |
| 2019/0008992 | A1 | 1/2019 | Kihm et al. |
| 2019/0366809 | A1* | 12/2019 | Fernandes ............... B60R 25/01 |
| 2020/0064322 | A1* | 2/2020 | Park ................... G01N 33/0031 |
| 2020/0218415 | A1* | 7/2020 | Jang ........................ G06N 3/08 |
| 2021/0302347 | A1 | 9/2021 | Hashizume |

FOREIGN PATENT DOCUMENTS

| | | |
|---|---|---|
| JP | 2018-088372 A | 6/2018 |
| JP | 2018161504 A | 10/2018 |
| JP | 6508689 B2 | 5/2019 |
| JP | 2019168887 A * | 10/2019 |
| JP | 6768981 B1 | 10/2020 |
| KR | 10-1689763 B1 | 12/2016 |
| KR | 20200092468 A | 8/2020 |
| WO | 2018-168672 A1 | 9/2018 |

OTHER PUBLICATIONS

Ohsaki, Kazuhiko, Relation of taste nature of food and recent technology of flavor analysis, Fragrance Preference and Flavor Development, 2006, pp. 127-131, No. 230, ISSN: 0368-6558.
Japanese Notice of Reasons for Refusal, Application No. 2022-503231, Date of Drafting: Aug. 1, 2023, 11 pages.
Korean Office Action dated May 30, 2024, Korean Patent Application No. 10-2022-7032706 with English Translation, 18 pages.
European Patent Office Action, Application No. 21 760 590.6, dated Dec. 12, 2023, 7 pages, Netherlands.
Xinxia, Cai et al., A novel odour sensor coated with a lipid membrane, Sensors and Actuators B: Chemical, Mar. 15, 1993, pp. 15-18, vol. 12, No. 1, China.

* cited by examiner

FIG.4

| ODOR INFORMATION | PREFERENCE INFORMATION | USER INFORMATION | | | |
|---|---|---|---|---|---|
| KIND | LIKE/DISLIKE | AGE | GENDER | AREA | |
| A | LIKE | 20 | FEMALE | FUKUOKA | ... |
| A | LIKE | 50 | MALE | FUKUOKA | ... |
| A | DISLIKE | 63 | MALE | YAMAGUCHI | ... |
| ... | ... | ... | ... | ... | ... |
| B | LIKE | 32 | FEMALE | SAGA | ... |
| B | DISLIKE | 45 | MALE | NAGASAKI | ... |
| B | DISLIKE | 63 | FEMALE | HIROSHIMA | ... |
| ... | ... | ... | ... | ... | ... |
| C | DISLIKE | 44 | FEMALE | SAGA | ... |
| C | DISLIKE | 50 | MALE | NAGASAKI | ... |
| C | DISLIKE | 21 | MALE | HIROSHIMA | ... |
| ... | ... | ... | ... | ... | ... |

FIG.12

| ODOR INFORMATION | PREFERENCE INFORMATION | USER INFORMATION | | | | ENVIRONMENTAL INFORMATION | | | |
|---|---|---|---|---|---|---|---|---|---|
| KIND | LIKE/DISLIKE | AGE | GENDER | AREA | ... | TEMPERATURE | HUMIDITY | WEATHER | ... |
| A | LIKE | 20 | FEMALE | FUKUOKA | ... | 15°C | 20% | FINE | ... |
| A | LIKE | 50 | MALE | FUKUOKA | ... | 30°C | 60% | CLOUDY | ... |
| A | DISLIKE | 63 | MALE | YAMAGUCHI | ... | 25°C | 50% | CLOUDY | ... |
| ... | ... | ... | ... | ... | ... | ... | ... | ... | ... |
| B | LIKE | 32 | FEMALE | SAGA | ... | 15°C | 30% | RAIN | ... |
| B | DISLIKE | 45 | MALE | NAGASAKI | ... | 25°C | 60% | CLOUDY | ... |
| B | DISLIKE | 63 | FEMALE | HIROSHIMA | ... | 5°C | 10% | SNOW | ... |
| ... | ... | ... | ... | ... | ... | ... | ... | ... | ... |
| C | DISLIKE | 44 | FEMALE | SAGA | ... | 15°C | 20% | RAIN | ... |
| C | DISLIKE | 50 | MALE | NAGASAKI | ... | 30°C | 40% | CLOUDY | ... |
| C | DISLIKE | 21 | MALE | HIROSHIMA | ... | 25°C | 60% | FINE | ... |
| ... | ... | ... | ... | ... | ... | ... | ... | ... | ... |

INFORMATION MANAGEMENT SYSTEM, INFORMATION MANAGEMENT METHOD, AND PROGRAM

CROSS-REFERENCE TO RELATED APPLICATIONS

This application is a national phase application of International Patent Application No. PCT/JP2021/004580, filed Feb. 8, 2021, which claims priority to Japanese Patent Application No. 2020-034043, filed Feb. 28, 2020, the disclosures of which are hereby incorporated by reference in their entirety.

TECHNICAL FIELD

The present disclosure relates to an information management system, an information management method, and a program.

BACKGROUND ART

Odor sensors that sense odors are used in various places (for example, see Patent Literature 1). When such odor sensors are used, odorants that allow humans to sense odors can be qualitatively or quantitatively determined.

CITATION LIST

Patent Literature

Patent Literature 1: Japanese Patent No. 6508689

SUMMARY OF INVENTION

Technical Problem

There are various odors such as those allowing humans to experience better feelings, or to experience feelings of repulsion. Even in the case of the same odor, whether the odor is loved or hated depends on the person. A difference in the age, gender, physical condition of the person, or in culture to which the person belongs is known is one of the causes of the different ways of feeling for the same odor. Such an odor is an element essential for social life, and therefore, it is important to reveal a relationship between a difference in the way of feeling for an odor and the cause of the difference. However, the fact of the matter is that a mechanism for analyzing the relationship between the difference in way of feeling for an odor and the cause of the difference has not yet been provided.

The present disclosure was made under such actual circumstances with an objective to provide an information management system, an information management method, and a program, capable of obtaining data on which a mechanism for analyzing a relationship between a difference in the way of feeling for an odor and the cause of the difference is based.

Solution to Problem

In order to achieve the objective described above, an information management system according to a first aspect of the present disclosure includes:
an odor sensor to sense an odor;
a user information acquirer to acquire user information indicating the attribute of a user;
a preference information inputter into which preference information indicating a preference of the user for the odor sensed by the odor sensor is input; and
a storage associates odor information indicating a kind of the odor sensed by the odor sensor, the user information acquired by the user information acquirer, and the preference information input into the preference information inputter with each other, and stores the odor information, the user information, and the preference information.

In such a case, it is also acceptable that:
the user information includes at least one piece of information of an age, gender, area, body type, living environment, occupation, hobby, and physical condition of the user.

It is also acceptable that:
the odor information includes strength of the odor.

It is also acceptable to further include an environmental information acquirer to acquire environmental information on space in which the odor drifts,
wherein the storage associates the odor information, the user information, and the preference information with the environmental information acquired by the environmental information acquirer, and stores the odor information, the user information, the preference information, and the environmental information.

It is also acceptable that:
the environmental information includes at least one piece of information of temperature, humidity, air pressure, weather, and positional information.

It is also acceptable to further include a biometric information acquirer to sense biometric information on the user,
wherein the storage associates the odor information, the user information, and the preference information with the biometric information sensed by the biometric information acquirer, and stores the odor information, the user information, the preference information, and the biometric information.

It is also acceptable that:
the biometric information includes:
at least one piece of information of a body temperature, blood pressure, heart rate, electrocardiogram, brain wave, and respiratory sound of the user.

It is also acceptable to further include a distance sensor to sense information on a distance between the odor sensor and a source of the odor,
wherein the storage associates the odor information, the user information, and the preference information with the information on the distance, and stores the odor information, the user information, the preference information, and the information on the distance.

It is also acceptable to further include an imager to image the source of the odor,
wherein the storage associates the odor information, the user information, and the preference information with an image of the source, imaged by the imager, and stores the odor information, the user information, the preference information, and the image.

It is also acceptable to further include a time measurer to generate information on a date and time when the odor is sensed by the odor sensor,
wherein the storage associates the odor information, the user information, and the preference information with the information on the date and time, generated by the time measurer, and stores the odor information, the user information, the preference information, and the information on the date and time.

It is also acceptable to further include an estimator to estimate a preference of a novel user for an odor with reference to the information stored in the storage.

It is also acceptable that:
the user information acquirer and the preference information inputter are mounted in a portable terminal possessed by the user,
the storage is mounted in a server computer connected to the portable terminal through a communication network, and
the odor sensor is connected to the portable terminal.

An information management method according to a second aspect of the present disclosure includes:
sensing, by an odor sensor, an odor;
acquiring, by an information processing device, user information indicating an attribute of a user;
inputting, by the information processing device, preference information indicating a preference of the user for the sensed odor; and
associating, by the information processing device, odor information indicating a kind of the sensed odor, the acquired user information, and the input preference information with each other, and storing, by the information processing device, the odor information, the user information, and the preference information.

A program according to a third aspect of the present disclosure causes a computer to function as:
a user information acquirer to acquire user information indicating an attribute of a user;
a preference information inputter to input preference information indicating a preference of the user for an odor sensed by an odor sensor to sense the odor; and
a storage to associate odor information indicating a kind of the odor sensed by the odor sensor, the user information acquired by the user information acquirer, and the preference information input into the preference information inputter with each other, and to store the odor information, the user information, and the preference information.

Advantageous Effects of Invention

In accordance with the present disclosure, preference information indicating the preference of a user for an odor is associated with user information indicating the attribute of the user, and the preference information and the user information are stored in a storage. Such information becomes information representing a relationship between a difference in the way of feeling for the odor and the cause of the difference, and thus becomes basic information for analyzing the relationship therebetween. Thus, in accordance with the present disclosure, it is possible to obtain data on which a mechanism for analyzing the relationship between the difference in the way of feeling for the odor and the cause of the difference is based.

BRIEF DESCRIPTION OF DRAWINGS

FIG. 4 is a table setting forth an example of information accumulated in a storage;

FIG. 12 is a table setting forth an example of information accumulated in a storage in FIG. 10;

DESCRIPTION OF EMBODIMENTS

Figure 1:
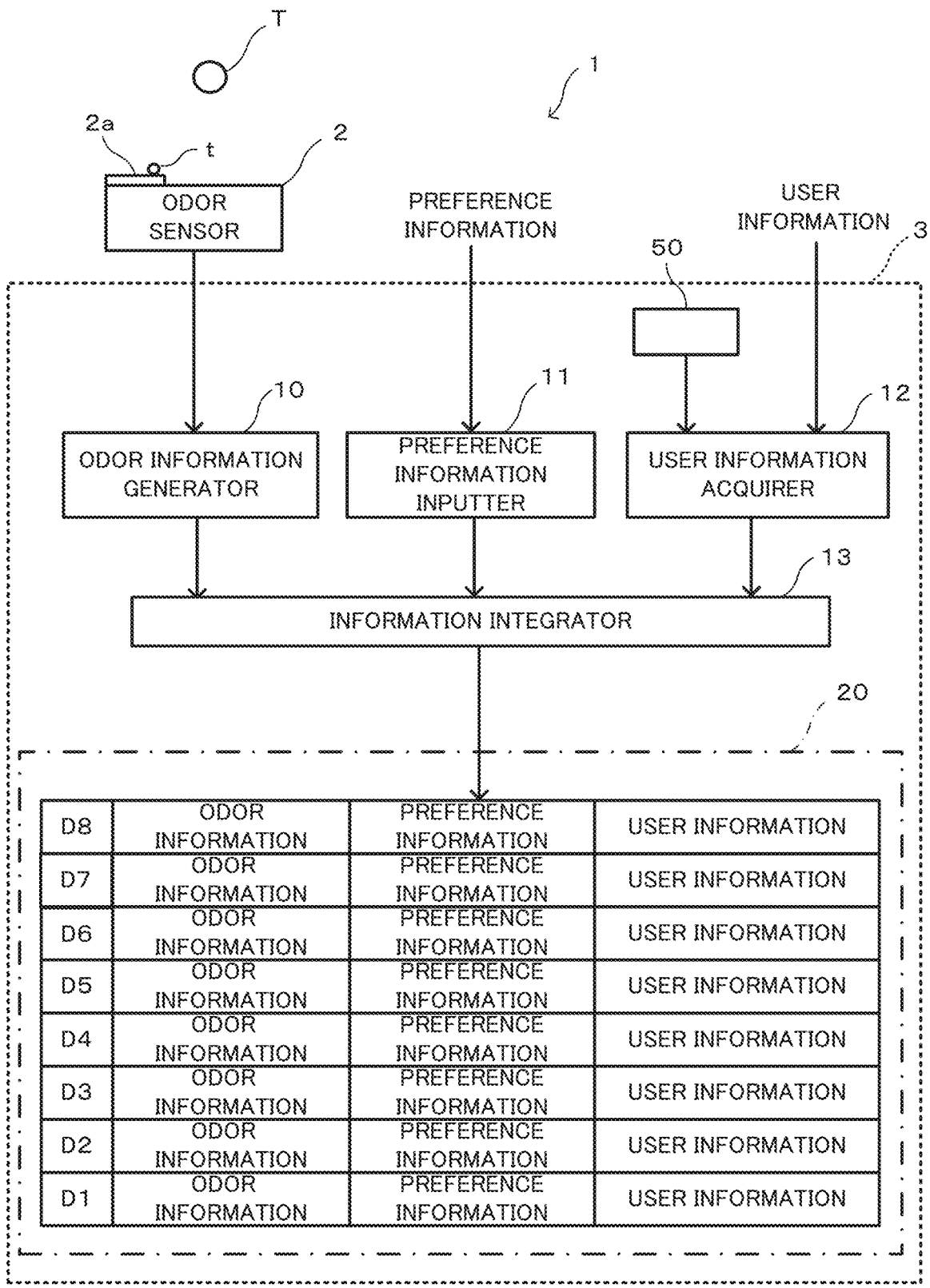
FIG. 1 is a block diagram illustrating the configuration of an information management system according to Embodiment 1 of the present disclosure.

Embodiments of the present disclosure are described in detail below with reference to the drawings. In each drawing, the same or similar portions are denoted by the same reference characters.

Embodiment 1

As illustrated in FIG. 1, an information management system 1 according to Embodiment 1 of the present disclosure includes an odor sensor 2 and an information processor 3.

The odor sensor 2 is a sensor to sense an odor, and is also referred to as a bad-smell sensor. Specifically, the odor sensor 2 is a sensitive membrane 2a that adsorbs an odorant t causing a person to feel an odor. Examples of the sensitive membrane 2a include various membranes such as a metal subjected to chemical modification, a metal oxide semiconductor, and a lipid membrane. In the present embodiment, a membrane including an acceptor allowed to adsorb the odorant t can be used as the sensitive membrane, and the kind of the membrane is not particularly limited.

The sensitive membrane 2a is inserted into a structure or an electric circuit, disposed in the odor sensor 2. When the odorant t is adsorbed onto the sensitive membrane 2a, the weight and the like of the sensitive membrane 2a are varied to change the physical properties of the structure including the sensitive membrane 2a or the electric circuit in which the sensitive membrane 2a is mounted. Examples of the physical properties of the structure include the vibration frequency, refractive index, fluorescence intensity, and temperature of the structure to which the sensitive membrane 2a is attached. Examples of the physical properties of the electric circuit including the sensitive membrane 2a include an electric conductivity, a resistance value, an impedance, a potential difference, and a capacitance. The odor sensor 2 senses an odor on the basis of a change in the physical properties of the structure or the electric circuit. The information management system 1 according to the present embodiment is not limited to the kinds of such physical properties.

The odor sensor 2 outputs a signal indicating a change in such a physical property. For example, when a source T emitting an odor is located nearby, and the odorant t emitted from the source T is adsorbed onto the sensitive membrane 2a, the level of the signal indicating the physical property of the sensitive membrane 2a is changed. Such a change in the level of the signal enables the adhesion of the odorant t to be sensed.

The odor sensor 2 may include plural kinds of sensitive membranes 2a, and may be capable of sensing several kinds of odorants t at once. The odor sensor 2 may include a cartridge in which a sensitive membrane 2a can be exchanged, and may be configured so that an odorant t that can be sensed can be changed by exchanging the cartridge. Such manners enable various odors to be sensed by the odor sensor 2.

There are also odors to which plural kinds of odorants t correspond, and which are necessarily specified by plural kinds of sensitive membranes 2a. In such a case, the odor sensor 2 senses and outputs signals indicating changes in physical properties in the plural kinds of the sensitive membranes 2a.

The information processor 3 is an information processing device to perform information processing. The information processor 3 is communicatably connected to the odor sensor 2. The information processor 3 inputs, from the odor sensor 2, a signal indicating a change in the physical property of the sensitive membrane 2a.

More specifically, the information processor 3 includes an odor information generator 10, a preference information inputter 11, a user information acquirer 12, an information integrator 13, and a storage 20, as illustrated in FIG. 1.

The odor information generator 10 inputs the signal indicating the change in the physical property of the sensitive membrane 2a, output from the odor sensor 2. The odor information generator 10 stores, in advance, information indicating the kind of an odor related to the odorant t adsorbed onto the sensitive membrane 2a. The odor information generator 10 associates the signal input from the odor sensor 2 with the information indicating the kind of the odor, and generates odor information indicating the kind of the odor sensed by the odor sensor 2.

As described above, the odor information generated by the odor information generator 10 basically includes the kind of the odor. There are various kinds of such odors. Examples of such odors include the odors of flowers, cosmetics, foods, drinks, body odors, and organisms. The kind of the odor may also be the odorant t itself. In the present embodiment, the kind of the odor is not particularly limited.

Figure 3:
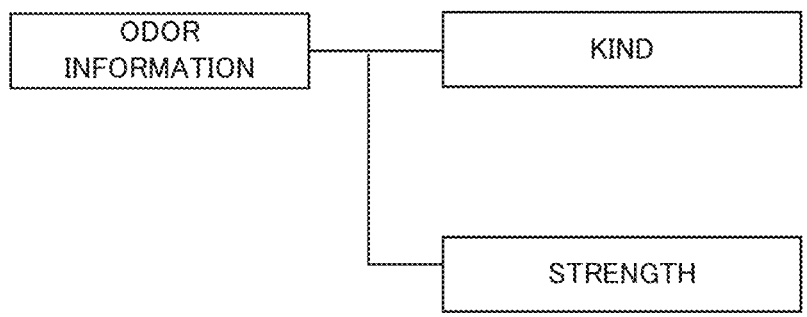
FIG. 3 is a tree diagram illustrating an example of the detailed items of odor information.

As illustrated in FIG. 3, the odor information may include the strength of an odor as well as the kind of the odor. The strength of the odor can be set depending on the amount of change in the physical property of the sensitive membrane 2a in a signal from the odor sensor 2. In other words, the odor can be regarded as strong in a case in which the amount of change in the physical property is more than a threshold value, while the odor can be regarded as weak in a case in which the amount is not more than the threshold value.

The odor sensor 2 may send, to the odor information generator 10, a signal including information on the kind of the sensed odorant t, that is, the kind of the odor. In such a case, the odor information generator 10 may preferably convert data indicated by the input signal into the form of information stored, as odor information indicating the kind of an odor, in the storage 20.

The preference information inputter 11 inputs preference information indicating the preference of a user for the odor sensed by the odor sensor 2. The preference information becomes information indicating whether the user likes or dislikes the odor. In the information processor 3, various man-machine interfaces into which the operation of a user can be input (see FIG. 7) are disposed as hardware, as described later. The preference information inputter 11 inputs the preference information through such a man-machine interface. In addition to the information indicating whether the odor is liked or disliked, information indicating neither may be included in the preference information.

Figure 2:
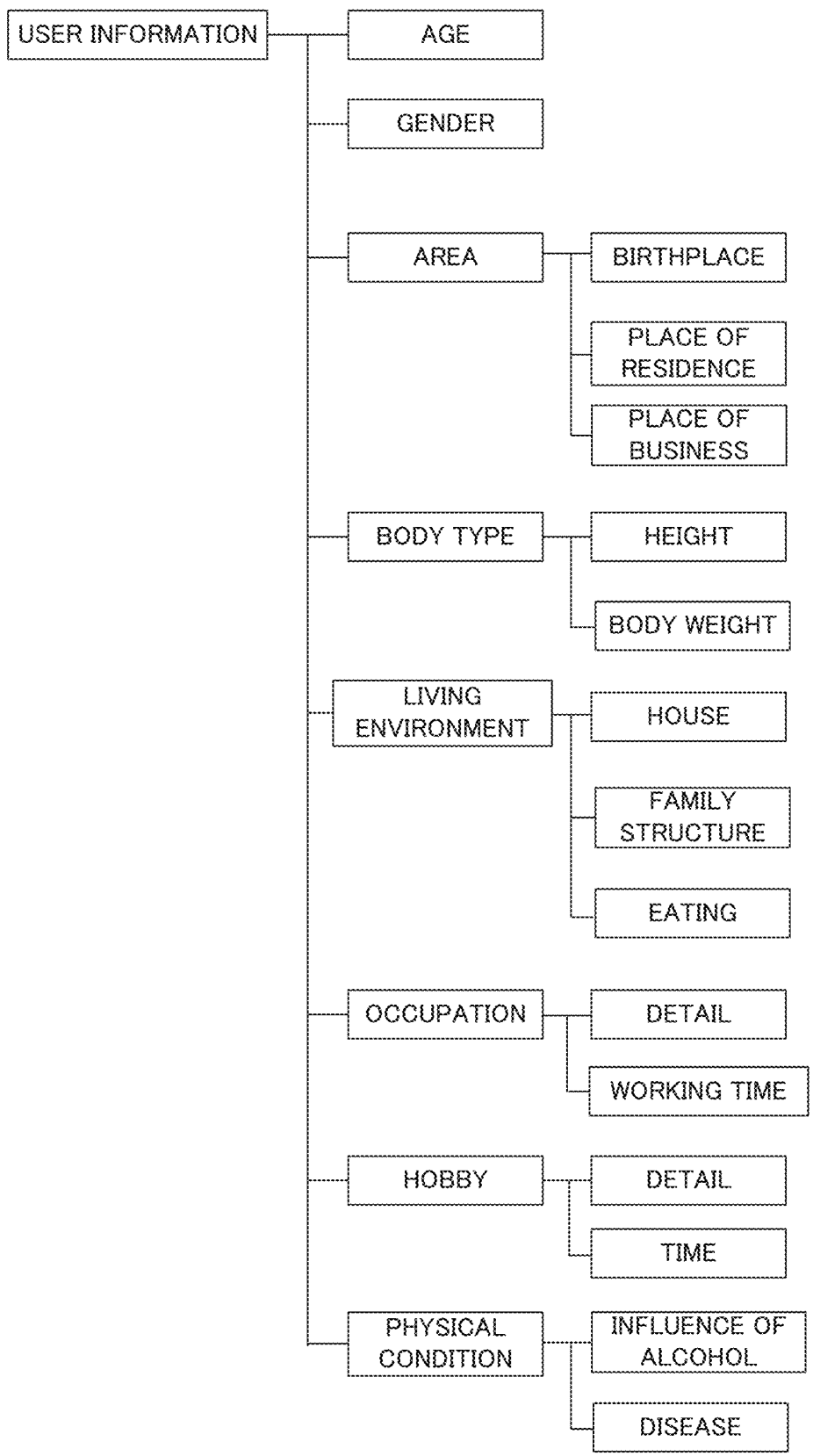
FIG. 2 is a tree diagram illustrating an example of the detailed items of user information.

The user information acquirer 12 acquires user information indicating the attribute of the user. The user information includes information indicating at least one of the age, gender, area, body type, living environment, occupation, hobby, and physical condition of the user, as illustrated in FIG. 2. The area is an area to which the user is deeply related. The area includes, for example, a birthplace, the place of residence, the place of business, and the like. The body type includes a height, a body weight, and the like. The living environment includes a house (an apartment or a detached house), a family structure, eating, and the like. The occupation includes the details thereof, working time (time per month, time per day, and overtime), and the like. The occupation may include information indicating the characteristics of the occupation, such as whether the occupation is desk work or heavy labor. Inoccupation, a student, and the like can also be included as the attributes of the occupation. The hobby includes the details of the hobby, and time spent in the hobby. The physical condition includes information such as whether the user has poor feeling, whether the user is under the influence of alcohol, and a contracted disease.

The user information is not limited to the information illustrated in FIG. 2. Any attributes possessed by an individual user can be included.

In the user information acquirer 12, inputting may be performed through such a man-machine interface as described above. The information processor 3 includes a user information storage 50, and the user information acquirer 12 may read and acquire user information from the user information storage 50 when the user information is stored in the user information storage 50 in advance. A current condition such as a physical condition is input through such a man-machine interface by a user.

The information integrator 13 inputs the odor information indicating the odor, generated by the odor information generator 10, the preference information input into the preference information inputter 11, and the user information acquired by the user information acquirer 12, associates the odor information, the preference information, and the user information, and integrates the odor information, the preference information, and the user information into one piece of information. The information integrator 13 allows the integrated information to be stored in the storage 20. Herein, "associate" means that a plurality of items of information is linked to each other in a state in which access can be made from one piece of information to the remaining items of information even when the plurality of items of information is accumulated together with the other information. In such a manner, for example, on the basis of specific user information, corresponding odor information and preference information can be accessed. Moreover, on the basis of odor information, corresponding user information and preference information can be accessed. Moreover, on the basis of preference information, corresponding odor information and user information can be accessed.

The storage 20 is a relational database. The storage 20 associates the odor information indicating the odor, generated by the odor information generator 10, the preference information input into the preference information inputter 11, and the user information acquired by the user information acquirer 12 with each other, and stores the odor information, the preference information, and the user information. FIG. 1 illustrates a situation in which items of integrated information to which identification numbers D1 to D8 are assigned are accumulated in the storage 20. When an identical identification number is assigned to items of information associated with each other in such a manner, the associated items of information can be extracted from many items of information. Such an identification number may be preferably a number unique to each piece of information.

The information integrator 13 may be absent. In this case, each of the odor information generator 10, the preference information inputter 11, and the user information acquirer 12 may write the odor information, the preference information, and the user information in the storage 20 in a corresponding storage area with an identical identification number.

For example, such items of information as illustrated shown in FIG. 4 is collected by the accumulation of such integrated information. FIG. 4 collectively sets forth the integrated information on the basis of an odor. For example, whether each of a plurality of users likes or dislikes any of odors, and the age, gender, area, and the like of each user are associated and stored based on each of the kinds A, B, and C of the odors.

Figure 5:
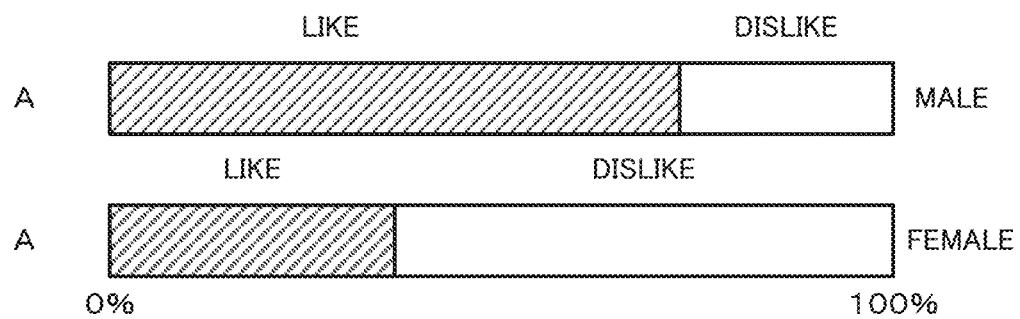
FIG. 5 is a view indicating, by gender, the percentages of persons who replied that the persons like a certain odor and persons who replied that the persons dislike the odor.
Figure 6:
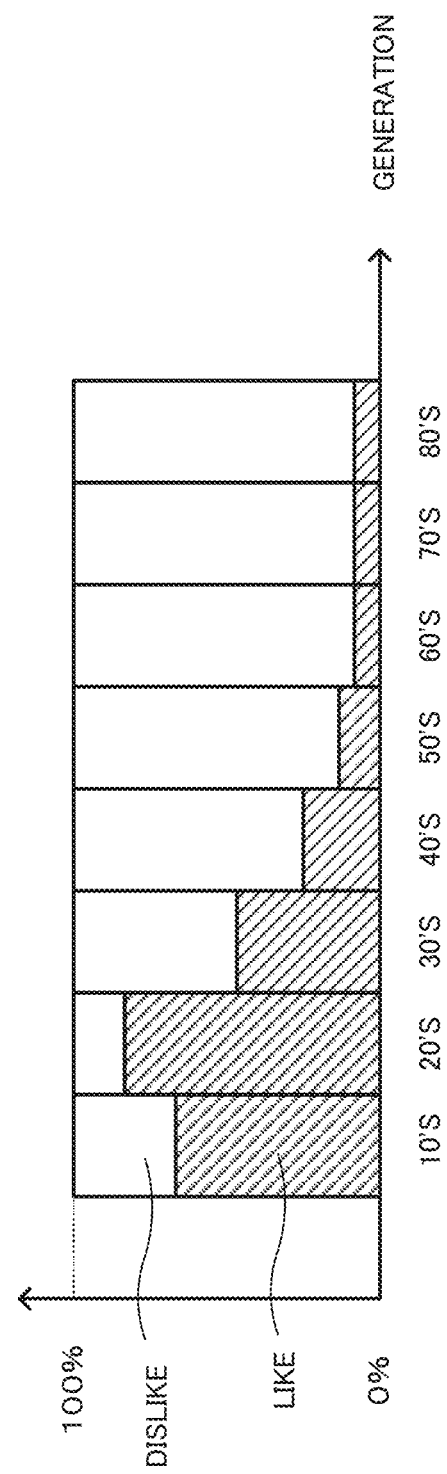
FIG. 6 is a view indicating, by generation, the percentages of persons who replied that the persons like a certain odor and persons who replied that the persons dislike the odor.

The various preferences of an individual for an odor can be analyzed based on information accumulated in the storage 20. For example, the percentages of persons who replied that the persons like an odor A and persons who replied that the persons dislike the odor A can be determined by gender, as illustrated in FIG. 5. As illustrated in FIG. 6, the percentages of the persons who replied that the persons like the odor A and the persons who replied that the persons dislike the odor A can be determined by generation. In addition, the percentage of persons who like or dislike an odor can be determined by area, body type, living environment, occupation, hobby, physical condition, or the like.

Figure 7:
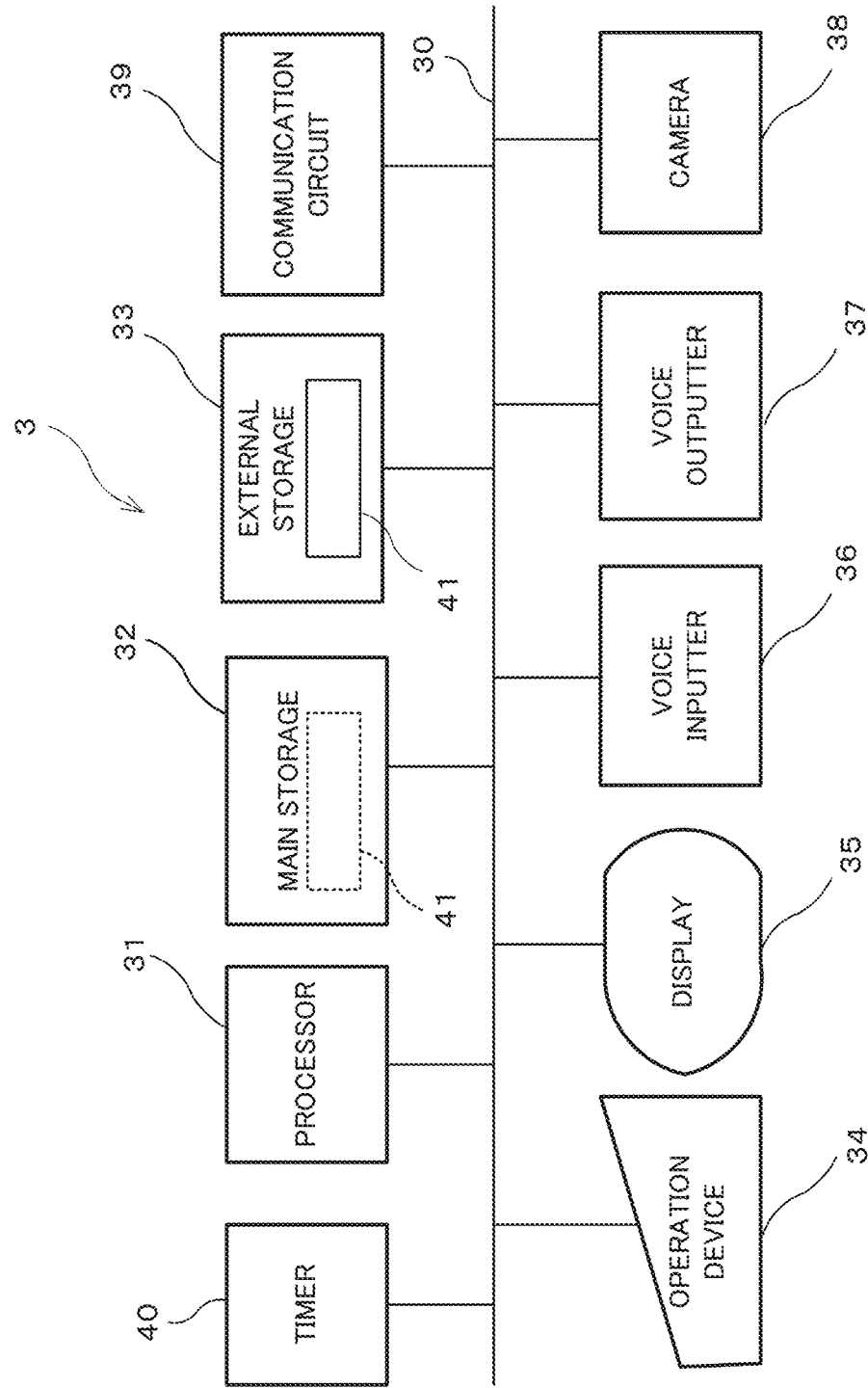
FIG. 7 is a block diagram illustrating the hardware configuration of an information processor in FIG. 1.

In order to implement the functions of the odor information generator 10, the preference information inputter 11, the user information acquirer 12, the information integrator 13, the storage 20, and the like as described above, the information processor 3 includes, as hardware, a processor 31, a main storage 32, an external storage 33, an operation device 34, a display 35, a voice inputter 36, a voice outputter 37, a camera 38, a communication circuit 39, and a timer 40, as illustrated in FIG. 7. All of the main storage 32, the external storage 33, the operation device 34, the display 35, the voice inputter 36, the voice outputter 37, the camera 38, the communication circuit 39, and the timer 40 are connected to the processor 31 through an internal bus 30.

The processor 31 is a unit that includes a central processing unit (CPU) and the like, and executes a program. The processor 31 executes the processing of the odor information generator 10, the preference information inputter 11, the user information acquirer 12, the information integrator 13, and the like according to a program 41 stored in the external storage 33, whereby the functions of the information processor 3 as the information processing device illustrated in FIG. 1 is implemented.

The main storage 32 includes random-access memory (RAM) and the like. A program 41 stored in the external storage 33 is loaded in the main storage 32. In addition, the main storage 32 is used as a work area for the processor 31 (temporary memory area for information).

The external storage 33 includes a nonvolatile memory such as a flash memory, a hard disk, a digital versatile disc random-access memory (DVD-RAM), or a digital versatile disc rewritable (DVD-RW). The program 41 to be executed by the processor 31 is stored in advance in the external storage 33. According to an instruction from the processor 31, the external storage 33 supplies information used in the case of executing the program 41 to the processor 31 and stores information supplied from the processor 31.

The operation device 34 includes a keyboard, a pointing device such as a mouse, and/or the like, as well as an interface device through which the keyboard, the pointing device, and/or the like are connected to the internal bus 30. Information on the details of operation by a user is input into the processor 31 through the operation device 34.

The display 35 includes a cathode ray tube (CRT), a liquid crystal display (LCD), or the like. A screen for the input is displayed when a user intends to input preference information or user information. The operation device 34 and the display 35 can also be integrated to make a touch panel.

The voice inputter 36 is a microphone for inputting the voice of a user, or the like. The voice inputter 36 is used in order for a user to input information by voice.

The voice outputter 37 is a speaker. The voice outputter 37 outputs voice or the like that prompts a user to input information. In the present embodiment, the operation device 34, the display 35, the voice inputter 36, and the voice outputter 37 correspond to the man-machine interfaces.

The camera 38 is a camera capable of imaging an image or video. The camera 38 is used for imaging the source T, as described later.

The communication circuit 39 is connected to a wireless or wired communication network. The communication circuit 39 is an interface circuit to communicate with another computer through the communication network. Examples of the communication network include a communication network 4, in FIG. 9, described later.

The timer 40 performs time measurement. When requiring current time information or information on current date and time, the processor 31 obtains time information or information on date and time, measured by the timer 40.

The operation of the information management system 1 according to the present embodiment is described with reference to a flow chart in FIG. 8.

Figure 8:
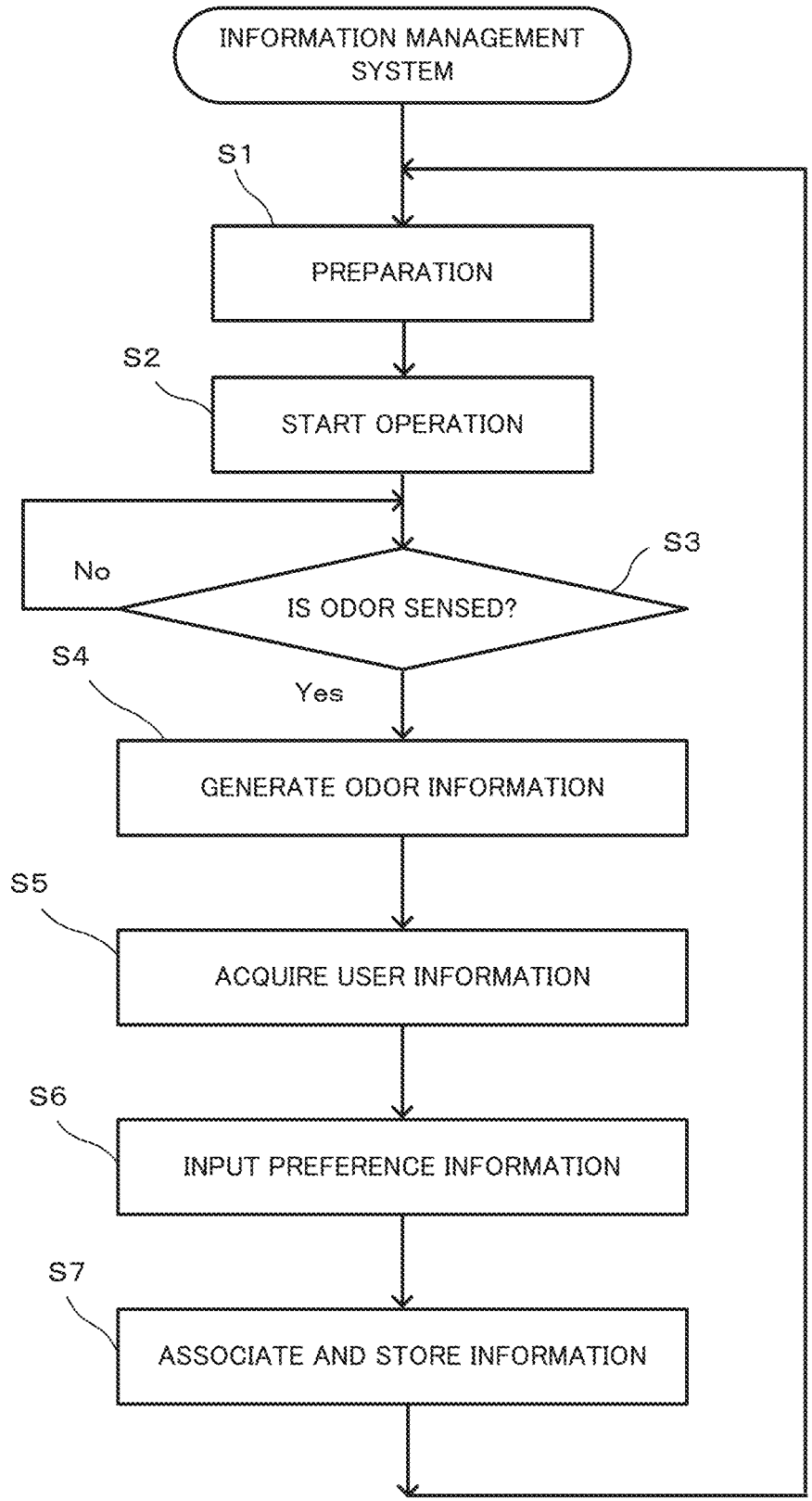
FIG. 8 is a flow chart illustrating the operation of the information management system in FIG. 1.

First, the information management system 1 performs a preparation for sensing an odor (step S1), as illustrated in FIG. 8. Herein, for example, the source T that emits an odor as a sample is prepared. It is not necessary to prepare such a source T in a place in which an odor has been present. Further, herein, the status of the odor sensor 2 is set to be a status in which an odor emitted from the source T can be sensed. The odor sensor 2 is reset in an initial state in which the odor sensor 2 can sense an odor by processing such as, for example, exchange of the cartridge of the odor sensor 2, or desorption of the odorant t that has already adhered from the sensitive membrane 2a.

At the end of the preparation of the sensing, the odor sensor 2 and the information processor 3 in the information management system 1 start operation (step S2). Specifically, the odor sensor 2 starts the output of a signal indicating a change in the physical property of the structure or electric circuit including sensitive membrane 2a. In contrast, the odor information generator 10 in the information processor 3 starts the input of a signal output from the odor sensor 2. In such a case, the level of the signal changed when the odorant t adheres to the sensitive membrane 2a. In such a manner, the odor sensor 2 senses the odor and outputs the signal indicating the change in the sensitive membrane 2a (odor sensing step).

Subsequently, the odor information generator 10 in the information processor 3 waits until the odor is sensed while monitoring the change in the level of the signal input from the odor sensor 2 (step S3; No). When the odor is sensed (step S3; Yes), the odor information generator 10 in the information processor 3 generates odor information on the basis of the signal input from the odor sensor 2 (step S4).

Subsequently, the user information acquirer 12 in the information processor 3 acquires user information indicating the attribute of a user (step S5; user information acquisition step). Specifically, the user information acquirer 12 allows an input image for user information to be displayed on the display 35 in the information processor 3. The input image is, for example, an image in which words prompting an age, a gender, a physical condition, and the like to be input are displayed, or an image for selecting the age, the gender, the physical condition, and the like. The user operates the operation device 34 to perform operation of inputting or selecting information such as an age, a gender, a physical condition, and the like while seeing the displayed input image.

When user information has already been stored in the user information storage 50, the user information acquirer 12 acquires the user information by reading the user information stored in the user information storage 50. It is also acceptable that the user is prompted to input the age, the gender, the physical condition, and the like by outputting voice from the voice outputter 37, and the user inputs information such as the age, the gender, the physical condition, and the like by inputting voice into the voice inputter 36.

Subsequently, the preference information inputter 11 in the information processor 3 inputs preference information indicating the preference of the user for the odor sensed in the odor sensing step described above (step S6; preference information input step). Specifically, the user information acquirer 12 allows an input image for preference information to be displayed on the display 35 in the information processor 3. The input image is, for example, an image for selecting whether the odor is liked or disliked. The user operates the operation device 34 to input whether the odor is liked or disliked while seeing the input image displayed on the display 35. It is also possible to output voice by the voice outputter 37 and to input voice by the voice inputter 36.

Subsequently, the information integrator 13 in the information processor 3 associates the odor information generated in step S4, the user information acquired in step S5, and the preference information input in step S6 with each other to generate the integration information thereof, and allows the integration information to be stored in the storage 20 (step S7; storing step). After the execution of step S7, the step goes back to step S1.

The steps S1 to S7 described above are repeated, integration information is accumulated in the storage 20 as the steps are repeated. The source T of an odor may be changed during the repetition. According to the change, the settings of the odor sensor 2 may be changed in step S1. Steps S4 to S6 are conducted in no particular order, and may be concurrently conducted.

Various analysis results can be obtained from the information accumulated in the storage 20. For example, it is found that a specific odor tends to be liked by males in a certain generation while the specific odor tends to be disliked by females in the same generation. It is possible to determine that, for example, persons in all the generations like or dislike a certain odor regardless of whether the persons are male or female. It is possible to determine that, as analysis results, for example, a preference for an odor is greatly changed depending on a body type, a living environment, an occupation, and a hobby, and the preference of even persons in the same generation and gender under the influence of alcohol, and a contracted disease, for an odor, is greatly changed. Such analysis results can be utilized in development of a product, holding of an event, and/or the like.

Embodiment 2

Figure 9:
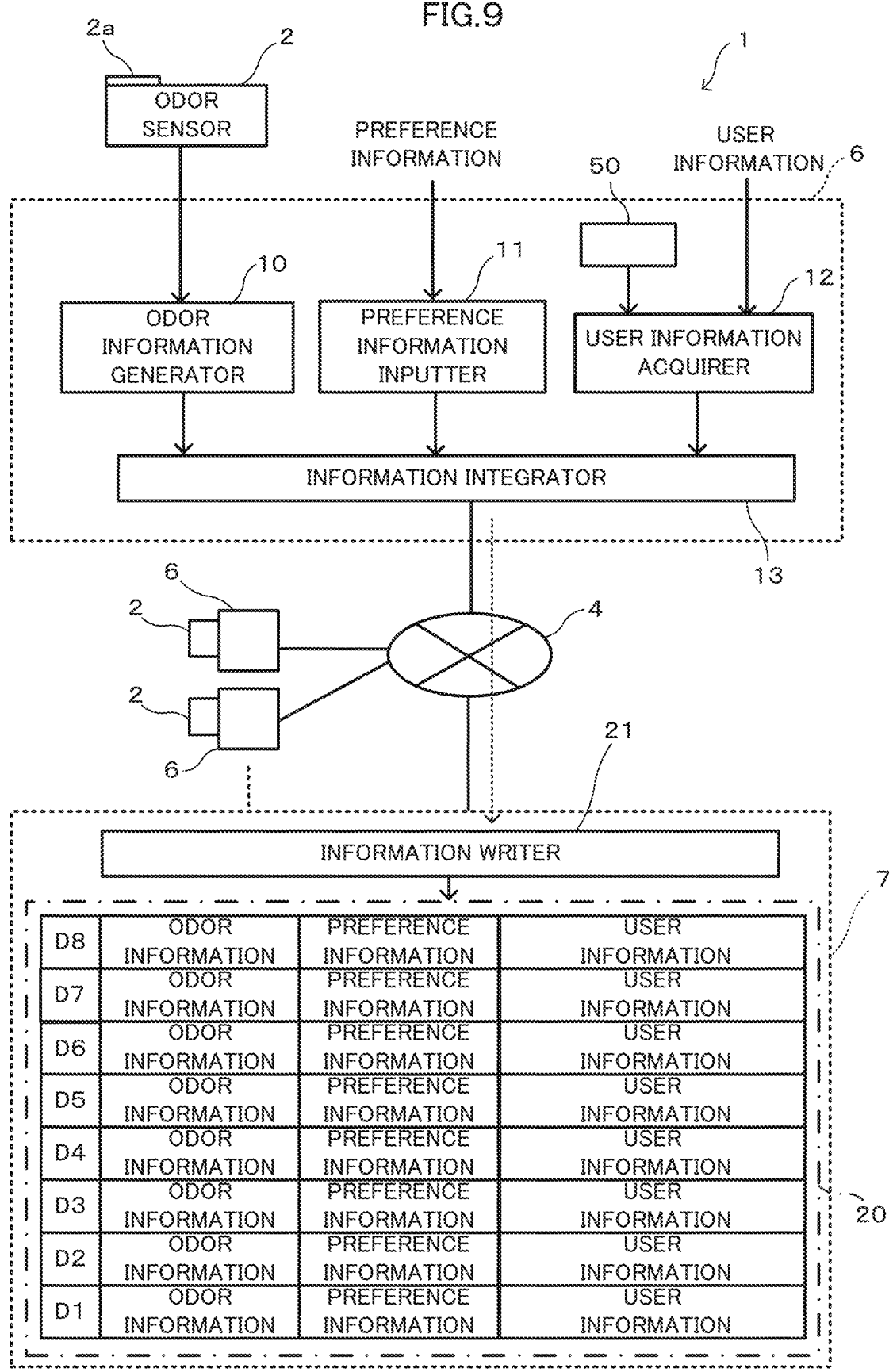
FIG. 9 is a block diagram illustrating the configuration of an information management system according to Embodiment 2 of the present disclosure.

Embodiment 2 of the present disclosure is now described. As illustrated in FIG. 9, a manner in which an information management system 1 according to the present embodiment includes an odor information generator 10, a preference information inputter 11, a user information acquirer 12, an information integrator 13, a storage 20, and a user information storage 50 is the same as that of the above-described information management system 1 according to Embodiment 1.

In the present embodiment, the odor information generator 10, the preference information inputter 11, the user information acquirer 12, and the information integrator 13 are mounted in a portable terminal 6 possessed by a user. Moreover, the storage 20 is mounted in a server computer 7 connected to the portable terminal 6 through a communication network 4. An odor sensor 2 is connected to the portable terminal 6.

In the present embodiment, the odor sensor 2 also senses an odor. In the portable terminal 6, the odor information generator 10 generates odor information from a signal input from the odor sensor 2. The preference information inputter 11 inputs preference information indicating the preference of the user the odor sensed by the odor sensor. The user information acquirer 12 acquires user information indicating the attribute of the user. The information integrator 13 associates the odor information, the preference information, and the user information with each other, and generates the integration information of the odor information, the preference information, and the user information. The information integrator 13 sends integration information to the server computer 7 through the communication network 4. In the present embodiment, the portable terminal 6 possessed by the individual user is used as an information processor. In such a portable terminal 6, user information related to many individual users is stored in the user information storage 50. The user information acquirer 12 can acquire the majority of the items of the user information from the user information storage 50.

The server computer 7 includes an information writer 21. The information writer 21 receives the integration information sent through the communication network 4. The information writer 21 allows the received integration information to be stored in the storage 20. In other words, the storage 20 associates the odor information generated by the odor information generator 10, the preference information input into the preference information inputter 11, and the user information acquired by the user information acquirer 12 with each other, and stores the odor information, the preference information, and the user information.

The hardware configuration of the portable terminal 6 and the server computer 7 is basically the same as the hardware configuration of the information processor 3 illustrated in FIG. 7. However, the voice inputter 36, the voice outputter 37, and the camera 38 are unnecessary in the server computer 7.

A plurality of portable terminals 6 of which the users are different from each other is connected to the communication network 4, and the odor sensor 2 is connected to each portable terminal 6. The user uses the portable terminal 6 and the odor sensor 2 to sense an odor and to input the preference information. The information integrator 13 of the portable terminal 6 sends the integration information, in which the odor information, the preference information, and the user information are integrated, to the server computer 7 through the communication network 4. The information writer 21 in the server computer 7 writes the integration information in the storage 20 to accumulate the information.

Collection of information using the portable terminal 6 that can be connected through the communication network 4 as described above enables information to be collected from a large number of users, and therefore enables the statistical reliability of the accumulated information to be improved. As a result, the accuracy of analysis results using the information can be allowed to be high.

In accordance with the present embodiment, since the portable terminal 6 is used, one can move to perform, for example, sensing of an odor anywhere.

Embodiment 3

Figure 10:
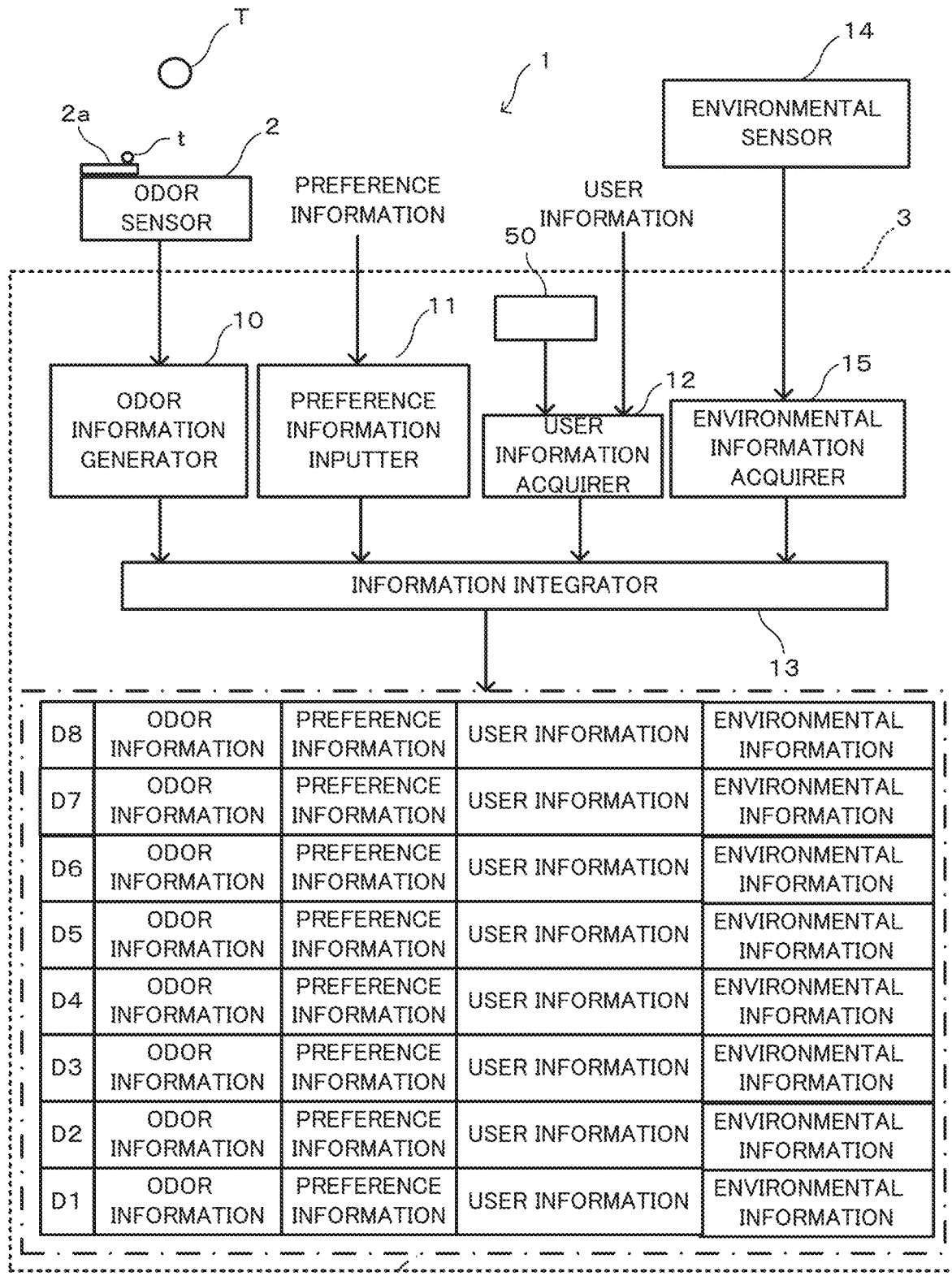
FIG. 10 is a block diagram illustrating the configuration of an information management system according to Embodiment 3 of the present disclosure.

Embodiment 3 of the present disclosure is now described. As illustrated in FIG. 10, the configuration of an information management system 1 according to the present embodiment is the same as that of the information management system 1 according to Embodiment 1 as described above in view of including an odor sensor 2 and an information processor 3. The information management system 1 further includes an environmental sensor 14. The environmental sensor 14 senses environmental information on space in which an odor drifts.

Figure 11:
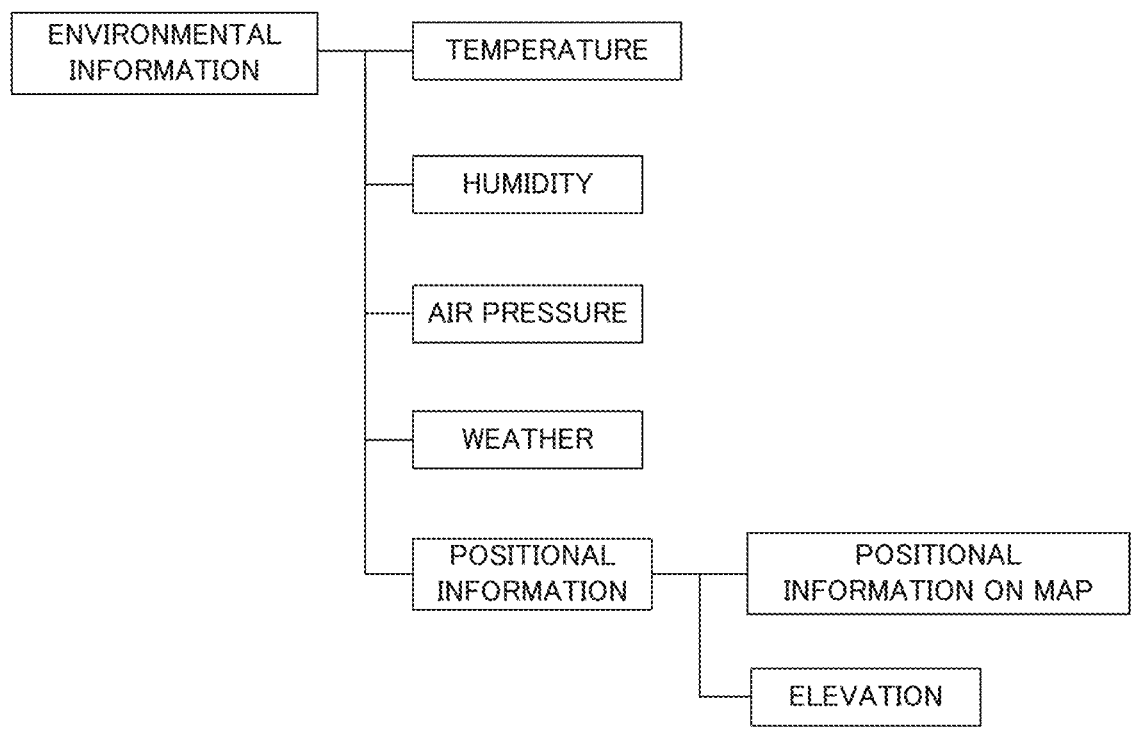
FIG. 11 is a tree diagram illustrating an example of the detailed items of environmental information.

The environmental sensor 14 is connected to the information processor 3. The environmental information includes at least one piece of information of temperature, humidity, air pressure, weather, and positional information, as illustrated in FIG. 11. The positional information includes elevation information as well as positional information on a map (planar map). However, the environmental information is not limited thereto. For example, information on airborne pollen counts, information on the density of PM 2.5, or information on photo-chemical smog may be included.

The information processor 3 includes an environmental information acquirer 15. The environmental information acquirer 15 acquires the environmental information sensed by the environmental sensor 14. An information integrator 13 associates odor information generated by an odor information generator 10, user information acquired by a user information acquirer 12, preference information input into a preference information inputter 11, and the environmental information acquired by the environmental information acquirer 15 with each other to generate integration information, and allows the integration information to be stored in a storage 20.

For example, information as set forth in FIG. 12 is stored in the storage 20. In such a manner, it is possible to statistically recognize how a plurality of users feels a certain odor, for example, when temperature and humidity are in predetermined ranges, and weather is fine.

The manner of feeling of a person for an odor depends on an environment such as temperature or humidity at the time that the person feels the odor. Therefore, when the preference information on whether the odor is liked or disliked is associated with the environmental information, and the preference information and the environmental information are stored and accumulated, how an environment influences the manner of the feeling of the person for the odor can be analyzed based on the accumulated information.

For example, it is possible to obtain findings that even a certain odor liked by many males in a specific generation in a state in which humidity is low is liked by a decreased number of persons in a high-humidity state.

Actually, the environmental sensor 14 need not be disposed. In such a case, the environmental information acquirer 15 may acquire the environmental information by input operated by a user, or may acquire the environmental information through a communication network 4 (see FIG. 9).

In the present embodiment, the processor 31 in FIG. 7 executes the program 41 to thereby implement the function of the environmental information acquirer 15.

Embodiment 4

Figure 13:
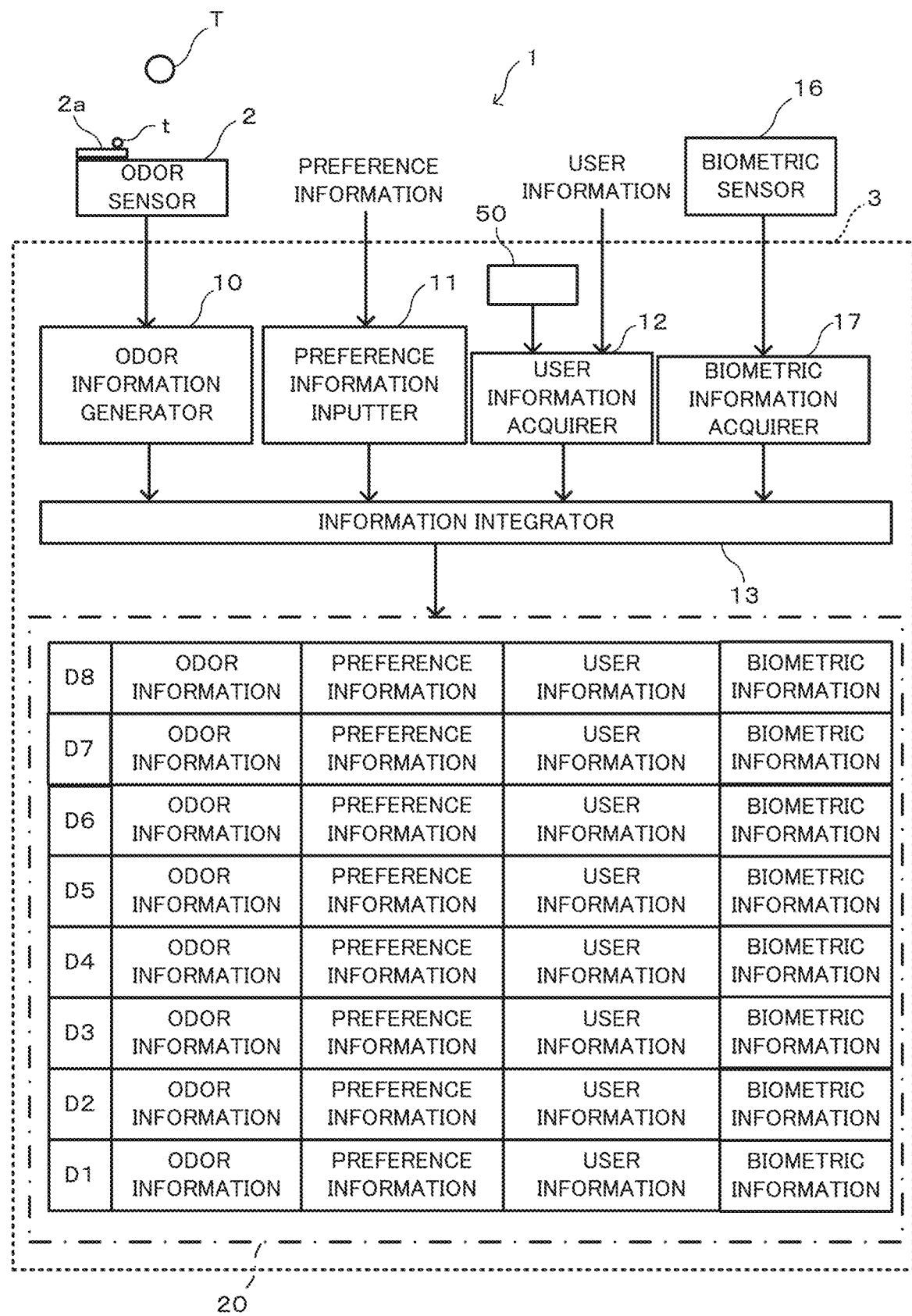
FIG. 13 is a block diagram illustrating the configuration of an information management system according to Embodiment 4 of the present disclosure.

Embodiment 4 of the present disclosure is now described. The configuration of an information management system 1 according to the present embodiment is the same as that of the information management system 1 according to Embodiment 1 as described above in view of including an odor sensor 2 and an information processor 3, as illustrated in FIG. 13. The information management system 1 further includes a biometric sensor 16. The biometric sensor 16 senses the biometric information of a user.

Figure 14:
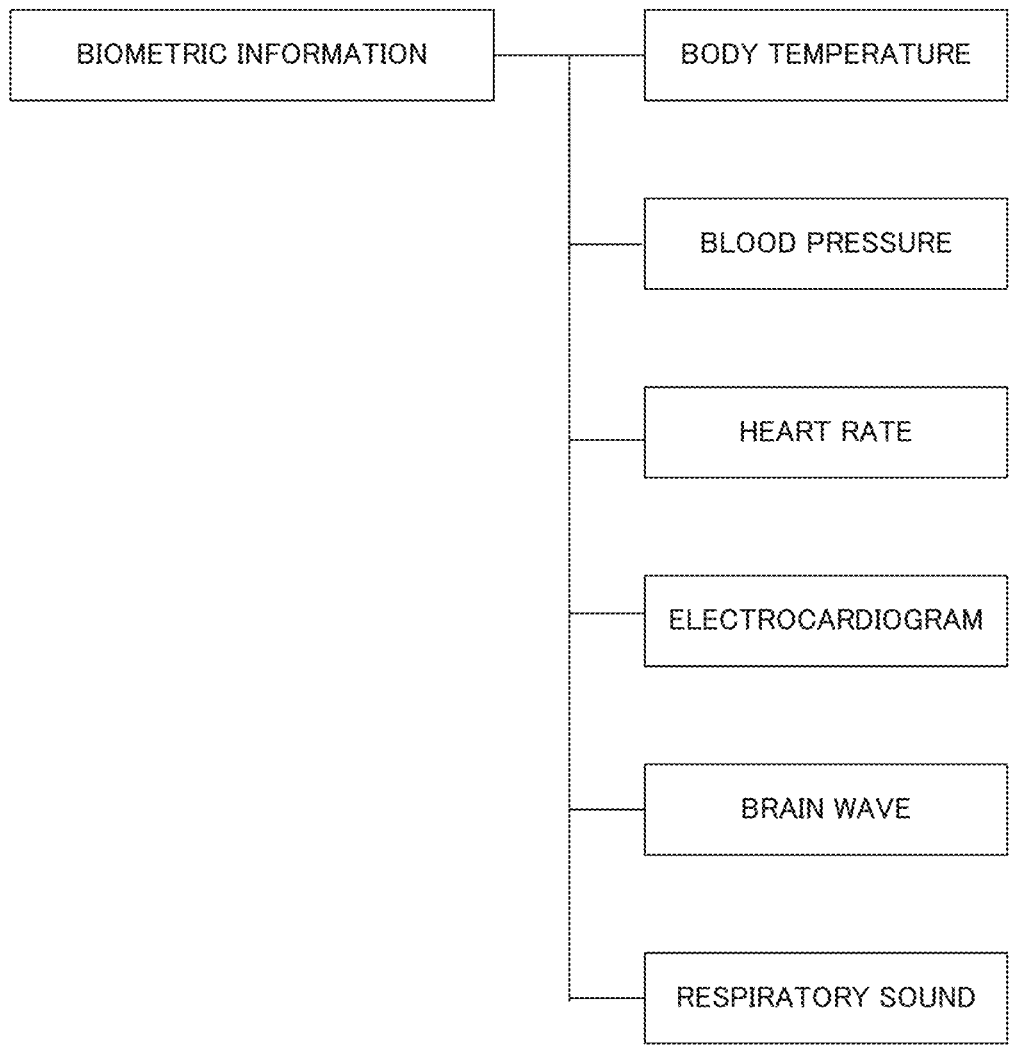
FIG. 14 is a tree diagram illustrating an example of the detailed items of biometric information.

The biometric sensor 16 is connected to the information processor 3. The biometric information includes at least one piece of information of a body temperature, a blood pressure, a heart rate, an electrocardiogram, a brain wave, and a respiratory sound, as illustrated in FIG. 14. However, the biometric information is not limited thereto. All the indicators of the health condition of a human body, which can be observed in the human body can be included.

The information processor 3 includes a biometric information acquirer 17. The biometric information acquirer 17 acquires the biometric information of the user, sensed by the biometric sensor 16. The information integrator 13 associates odor information generated by an odor information generator 10, user information acquired by a user information acquirer 12, and preference information input into a preference information inputter 11 with the biometric information sensed by the biometric information acquirer 17 to generate integration information, and allows the integration information to be stored in a storage 20.

It is possible to statistically recognize how a user having, for example, a body temperature of 38° C. or more feels a certain odor with reference to the information stored in the storage 20.

The manner of feeling of a person for an odor also depends on the health condition of the body at the time that the person feels the odor. Therefore, when the preference information on whether the odor is liked or disliked is associated with the biometric information indicating the condition of the body, and the preference information and the biometric information are stored and accumulated, how the condition of the body influences the manner of the feeling of the person for the odor can be analyzed based on the accumulated information.

For example, it is possible to obtain findings that even a certain odor liked by many males in a specific generation in a good physical condition is liked by a decreased number of persons in a bad physical condition.

Actually, the biometric sensor 16 need not be disposed. In such a case, the biometric information acquirer 17 may acquire biometric information by, for example, input operated by a user, or may acquire the biometric information of the user from an external computer including the physical examination information of the user by information communications through a communication circuit 39 (FIG. 7).

In the present embodiment, the processor 31 in FIG. 7 executes the program 41 to implement the function of the biometric information acquirer 17.

Embodiment 5

Figure 15:
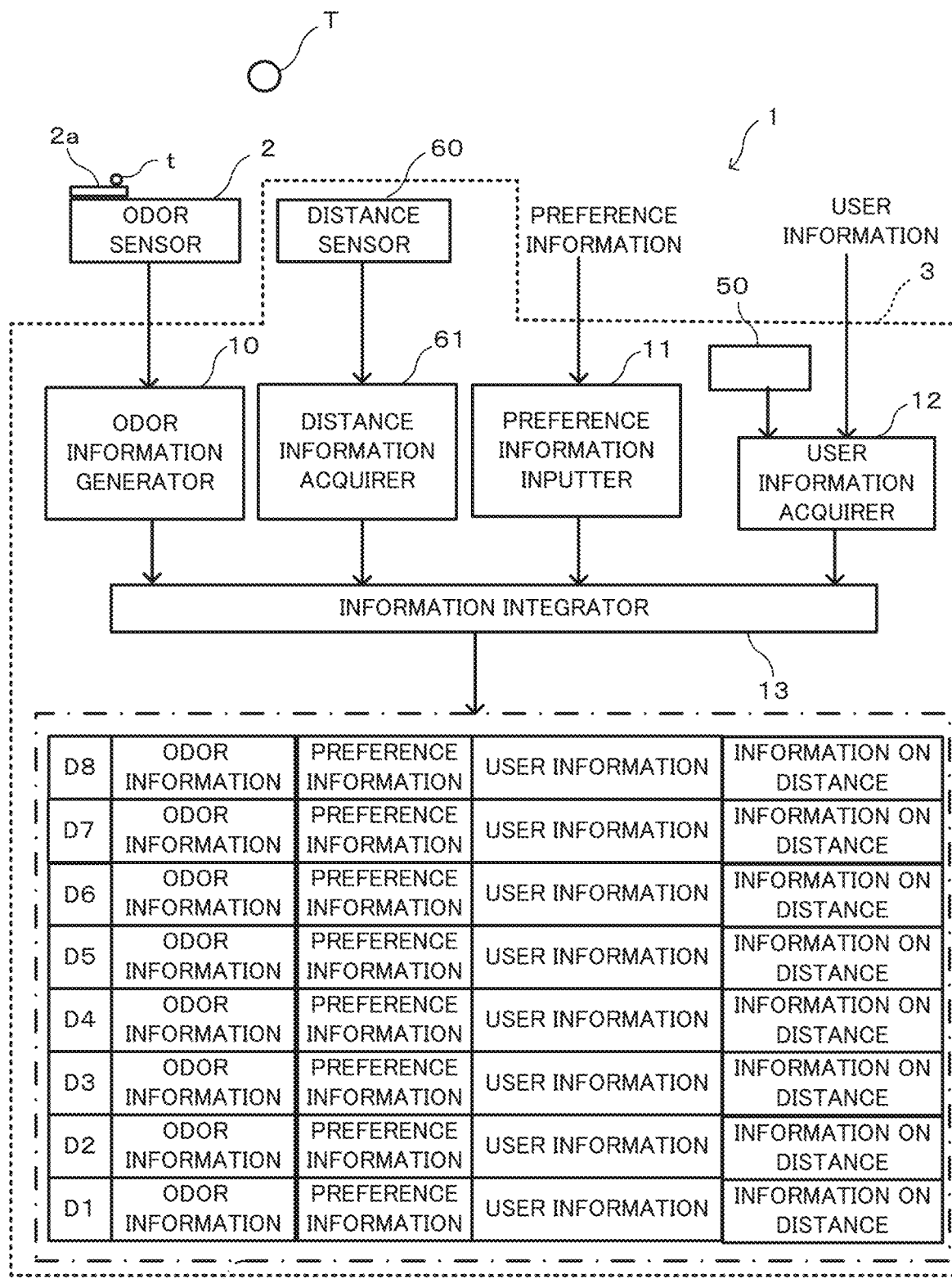
FIG. 15 is a block diagram illustrating the configuration of an information management system according to Embodiment 5 of the present disclosure.

Embodiment 5 of the present disclosure is now described. The configuration of an information management system 1 according to the present embodiment is the same as that of the information management system 1 according to Embodiment 1 as described above in view of including an odor sensor 2 and an information processor 3, as illustrated in FIG. 15. The information management system 1 further includes a distance sensor 60. The distance sensor 60 senses information on a distance between the odor sensor 2 and the source T of an odor.

The distance sensor 60 is connected to the information processor 3. The information processor 3 includes a distance information acquirer 61. The distance information acquirer 61 acquires the information on the distance, sensed by the distance sensor 60. An information integrator 13 associates odor information generated by an odor information generator 10, user information acquired by a user information acquirer 12, and preference information input into a preference information inputter 11 with the information on the distance, sensed by the distance information acquirer 61, to generate integration information, and allows the integration information to be stored in a storage 20.

Figure 16:
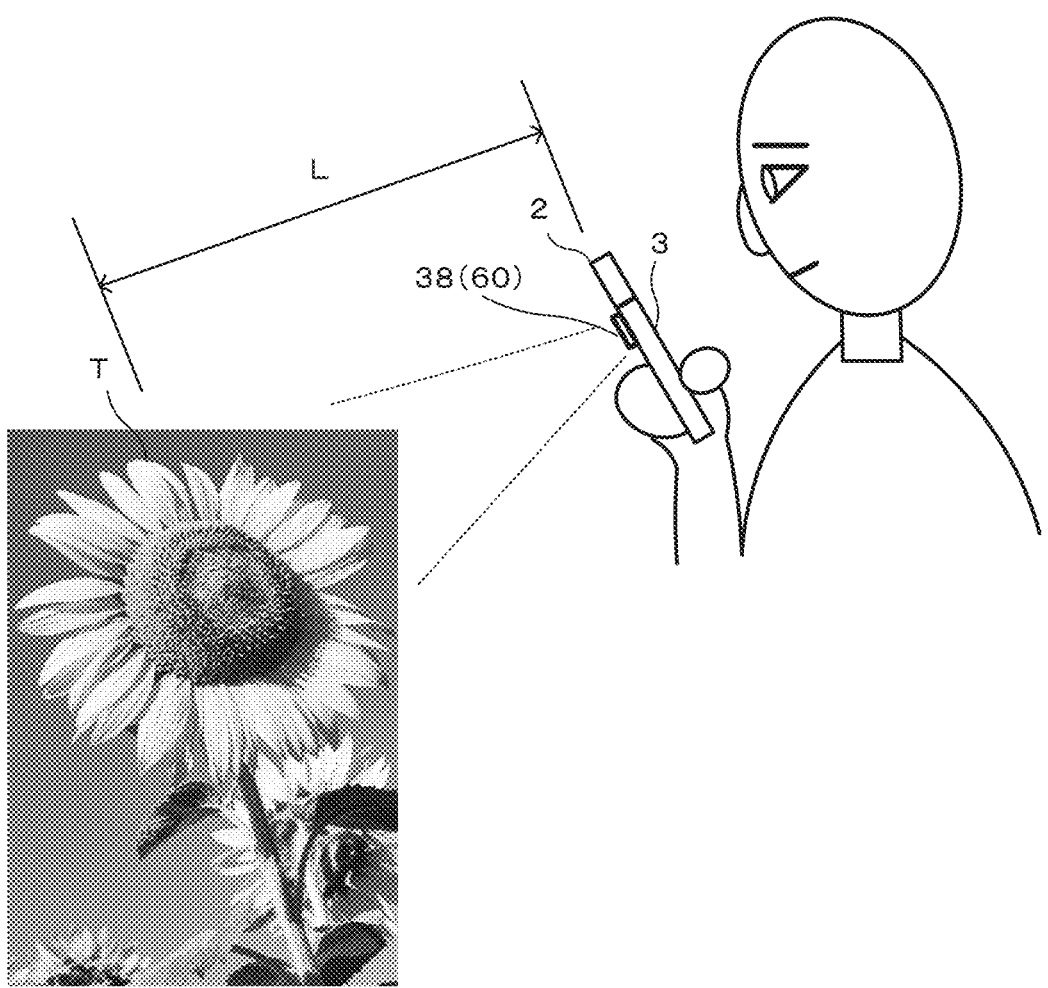
FIG. 16 is a view illustrating a situation in which the source of an odor is imaged by a camera.

A camera 38 (see FIG. 7) can be used as the distance sensor 60. As illustrated in FIG. 16, the camera 38 is placed adjacently to the odor sensor 2. Accordingly, the distance information acquirer 61 acquires the distance L (information on distance) between the odor sensor 2 and the source T of the odor on the basis of the image imaged with camera 38. The information on the distance need not be strict but may be expressed as a numerical value such as several meters or may be expressed as a representation such as "far" or "near". When the camera 38 is a compound eye camera, the distance can be precisely sensed based on a triangulation method.

When the information on the distance is associated and stored with the odor information, the preference information, and the user information in such a manner, it is possible to analyze the preference of a user for the odor, associated with the distance from the source T of the odor.

A sensor other than the camera may be used as the distance sensor 60. For example, an ultrasonic sensor and/or the like can be used.

In the present embodiment, a processor 31 in FIG. 7 executes a program 41 to thereby implement the function of the distance information acquirer 61.

Embodiment 6

Figure 17:
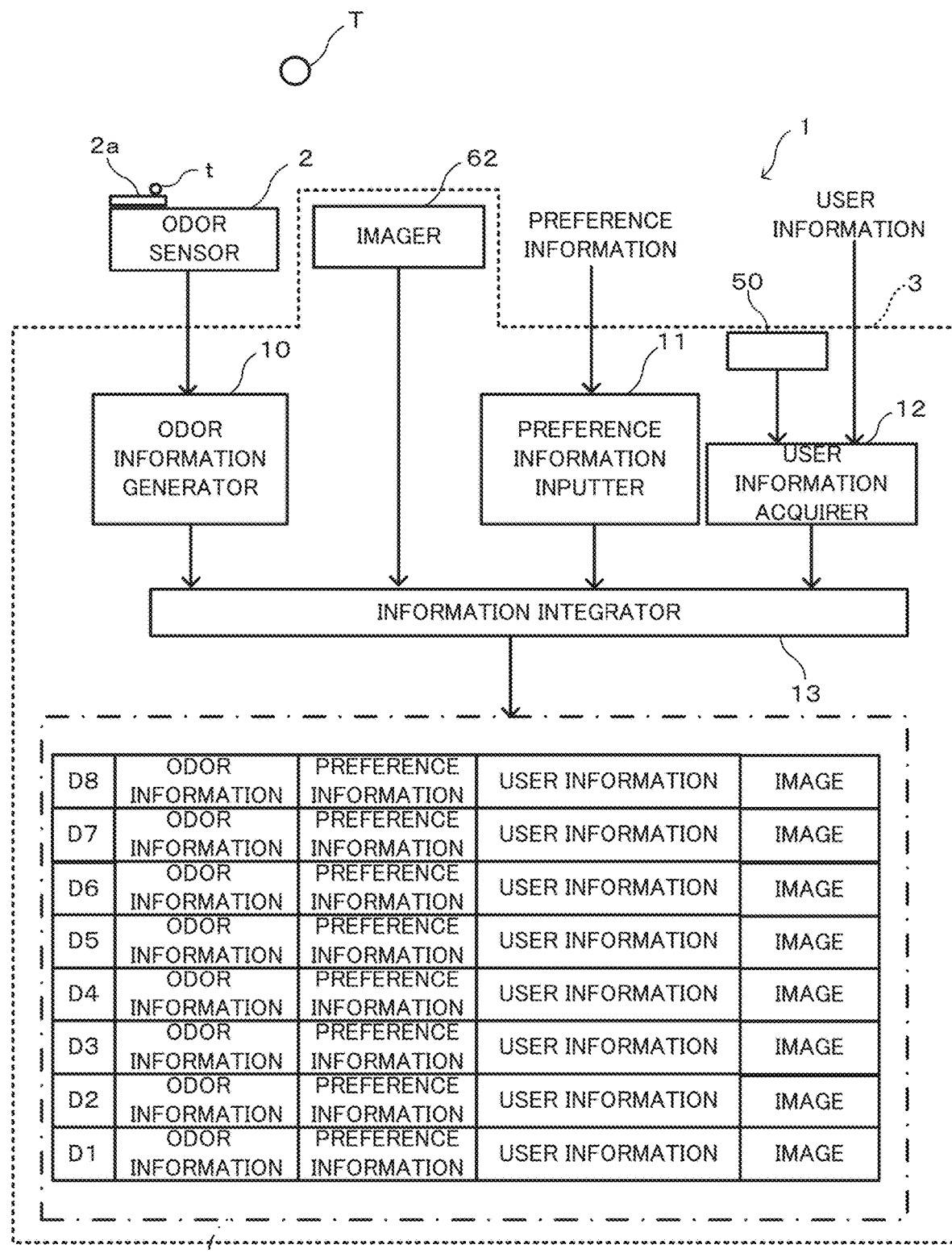
FIG. 17 is a block diagram illustrating the configuration of an information management system according to Embodiment 6 of the present disclosure.

Embodiment 6 of the present disclosure is now described. The configuration of an information management system 1 according to the present embodiment is the same as that of the information management system 1 according to Embodiment 1 as described above in view of including an odor sensor 2 and an information processor 3, as illustrated in FIG. 17.

The information management system 1 according to the present embodiment is different from the information management systems 1 according to the embodiments described above in view of including an imager 62. The imager 62 images the source T of an odor, as illustrated in FIG. 16. An information integrator 13 associates odor information generated by an odor information generator 10, user information acquired by a user information acquirer 12, and preference information input into a preference information inputter 11 with the image of the source T imaged by the imager 62, and allows the odor information, the user information, the preference information, and the image to be stored in a storage 20.

In such a manner, the odor information, the preference information, and the user information can be associated with the image of the source T of the odor to store the odor information, the preference information, the user information, and the image. In such a manner, it is possible to analyze, for example, how the state of the source T influences the manner of feeling of a person for the same odor.

In the present embodiment, a processor 31 in FIG. 7 executes a program 41 to control a camera 38, whereby the function of the imager 62 is implemented.

Embodiment 7

Figure 18:
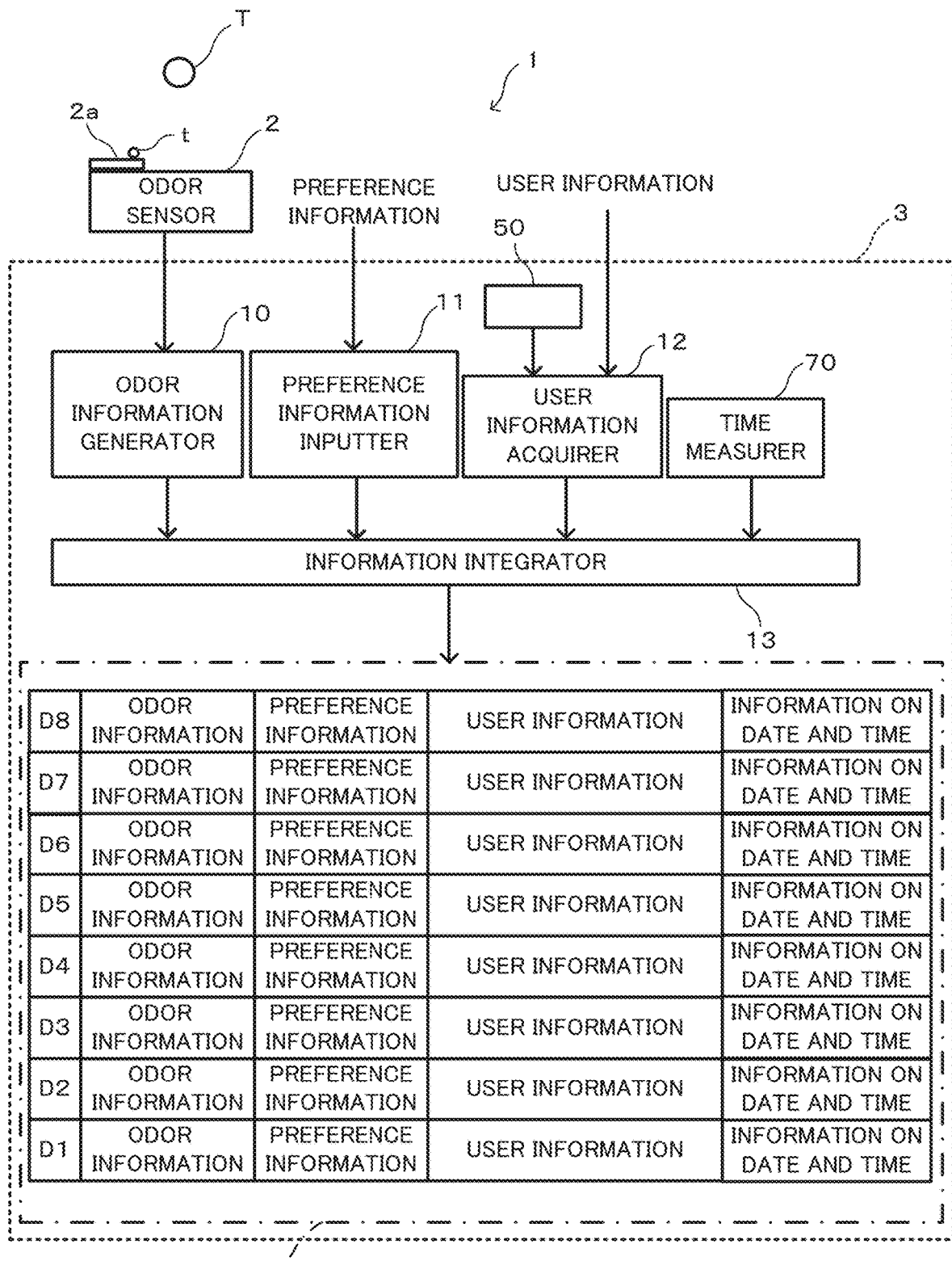
FIG. 18 is a block diagram illustrating the configuration of an information management system according to Embodiment 7 of the present disclosure.

Embodiment 7 of the present disclosure is now described. An information management system 1 according to the present embodiment is different from the information management systems 1 according to the embodiments described above in view of including a time measurer 70, as illustrated in FIG. 18.

The time measurer 70 measures time, that is, generates information on a date and time when an odor is sensed by an odor sensor 2. The information integrator 13 associates odor information generated by an odor information generator 10, user information acquired by a user information acquirer 12, and preference information input into a preference information inputter 11 with the information on the date and time measured by the time measurer 70, and allows the odor information, the user information, the preference information, and the information on the date and time to be stored in a storage 20.

The manner of feeling of a person for an odor also depends on a date and time. Accordingly, when the preference information on whether the odor is liked or disliked and the date and time when the odor is felt are associated with each other, stored, and accumulated, it is possible to analyze how a time period influences the manner of feeling of a person for an odor on the basis of the accumulated information.

In the present embodiment, a processor 31 in FIG. 7 executes a program 41 to read the information on the date and time from a timer 40, whereby the function of the time measurer 70 is implemented.

As described above, the environmental information, the biometric information, the information on a distance, the image, and the information on a date and time as well as the odor information, the preference information, and the user information are associated and stored in the embodiments described above. However, the present disclosure is not limited thereto. It is also acceptable to associate and store all or at least one of the biometric information, the information on the distance, the image, and the information on the date and time with the odor information, the preference information, and the user information.

Embodiment 8

Figure 19:
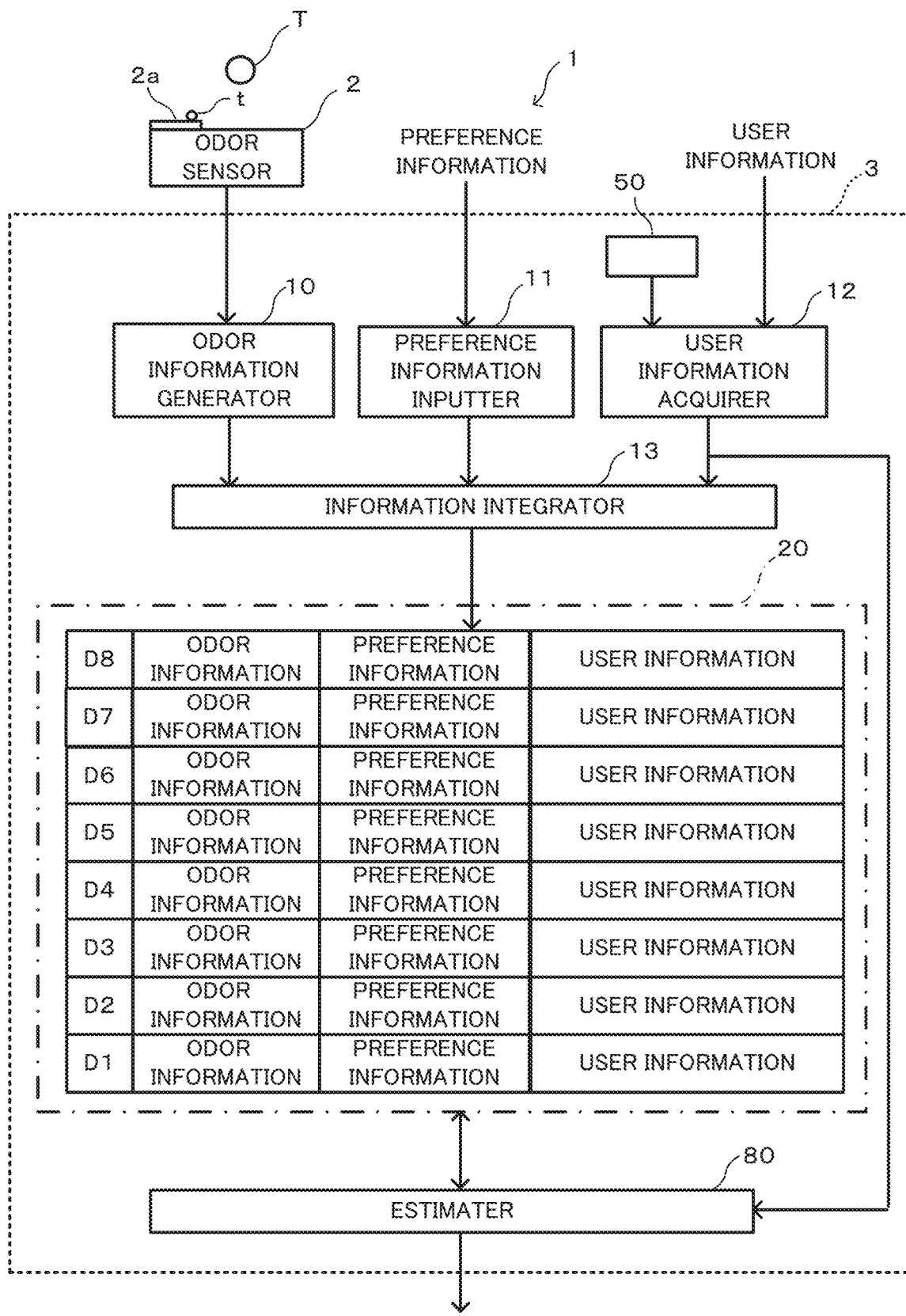
FIG. 19 is a block diagram illustrating the configuration of an information management system according to Embodiment 8 of the present disclosure.

Embodiment 8 of the present disclosure is now described. As illustrated in FIG. 19, an information management system 1 according to the present embodiment is different from the information management systems 1 according to the embodiments described above in view of including an estimator 80.

The estimator 80 inputs user information on a novel user from a user information acquirer 12. In the present embodiment, new integration information is not stored in a storage 20.

The estimator 80 estimates the preference of the novel user for an odor with reference to information stored in the storage 20. For example, when the age, gender, and the like of the novel user are input, the estimator 80 estimates odors liked and disliked by persons in the age group and gender, to which the novel user belongs, on the basis of a distribution related to odors in the same age groups and genders.

Estimation in the estimator 80 can be performed using various techniques. For example, the preference of a novel user for an odor can be estimated using a statistical technique. In this case, the estimation may be performed based on environmental information, biometric information, information on a distance, an image, and information on a date and time, as well as user information on the user. The estimator 80 may include a learning system in which machine learning and deep learning based on the information stored in the storage 20 are possible, to obtain estimated results by inputting the user information on the novel user, the environmental information, the biometric information, the information on the distance, the image, and the information on the date and time into the learning system.

In the present embodiment, a processor 31 in FIG. 7 executes a program 41 to thereby implement the function of the estimator 80.

The information management system 1 according to each of the embodiments described above can perform various analyses in relation to the manner of feeling of a person for an odor. For example, an odor liked by many persons in a certain age group who replied that the persons like the odor can be adopted as the odor of a product for the age group. An odor liked by many persons who replied that the persons like the odor regardless of an age, a gender, and the like can be adopted as an odor for an unspecified number of persons.

In accordance with the present embodiment, the preference information indicating whether the user likes or dislikes the odor is associated with the user information indicating the attribute of the user, and the preference information and the user information are stored as integrated information in the storage 20, as described in detail above. Such information becomes information representing a relationship between a difference in the way of feeling for the odor and the cause of the difference, and thus becomes basic information for analyzing the relationship therebetween. Thus, in accordance with the present embodiment, it is possible to obtain data on which a mechanism for analyzing the relationship between the difference in the way of feeling for the odor and the cause of the difference is based.

The configurations of the information management systems 1 described in Embodiments 3 to 8 as described above can be transformed to a configuration including a portable terminal 6 and a server computer 7, as illustrated in FIG. 9. In the information management system 1 according to Embodiment 8 as described above, the output of the estimator 80 may be transmitted to a portable terminal 6 possessed by a novel user.

The odor sensor 2 may be incorporated into the information processor 3. The same applies to the environmental sensor 14 and the biometric sensor 16.

In each of the embodiments described above, the number of an odor sensed at once is set at one. However, the present disclosure is not limited thereto. Two kinds or more of odors may be sensed at once. In this case, associated odor information related to the two kinds or more of the odors is stored in the storage 20.

Added information is not limited to environmental information, biometric information, information on a distance, an image of a source T, and information on a date and time. For example, a place in which an odor is sensed, and/or the like may be associated with integration information, and stored. All the causes of changing the manner of feeling for an odor can be included in the information.

The information processor 3 may be implemented using a common computer such as a portable terminal or a personal computer, as described above, or may be implemented as a dedicated device.

In addition, the hardware and software configurations of the information processor 3 are examples, and can be optionally changed and modified.

A portion that plays a key role in processing in the information processor 3 including the processor 31, the main storage 32, the external storage 33, the operation device 34, the display 35, the voice inputter 36, the voice outputter 37, the camera 38, the communication circuit 39, the timer 40, the internal bus 30, and the like can be implemented using a usual computer system without using a dedicated system, as described above. For example, the information processor 3 to execute the processing may be configured by distributing a computer program for executing the operation, stored in a non-transitory computer-readable recording medium (flexible disc, CD-ROM, DVD-ROM, or the like), and by installing the computer program on a computer. A usual computer system may, for example, download the computer program, stored in a storage included in a server device on a communication network such as the Internet, to configure the information processor 3.

Only an application program may be stored in a recording medium and a storage, for example, in the case of implementing the function of a computer by sharing between an operating system (OS) and the application program, or in cooperation between the OS and the application program.

A computer program can be superimposed on carrier waves, and distributed through a communication network. For example, the computer program may be posted on a bulletin board system (BBS) on the communication network to distribute the computer program through the network. It is also acceptable to make such a configuration may be made that the processing can be executed by starting the computer program and executing the computer program in a manner similar to that of another application program under the control of the OS.

The foregoing describes some example embodiments for explanatory purposes. Although the foregoing discussion has presented specific embodiments, persons skilled in the art will recognize that changes may be made in form and detail without departing from the broader spirit and scope of the invention. Accordingly, the specification and drawings are to be regarded in an illustrative rather than a restrictive sense. This detailed description, therefore, is not to be taken in a limiting sense, and the scope of the invention is defined only by the included claims, along with the full range of equivalents to which such claims are entitled.

This application claims priority based on Japanese Patent Application No. 2020-34043, filed on Feb. 28, 2020, the entire disclosure of which is incorporated by reference herein.

INDUSTRIAL APPLICABILITY

The present disclosure enables analysis of a difference in the preference of a user for an odor.

REFERENCE SIGNS LIST

1 Information management system
2 Odor sensor
2a Sensitive membrane
3 Information processor
4 Communication network
6 Portable terminal
7 Server computer
10 Odor information generator
11 Preference information inputter
12 User information acquirer
13 Information integrator
14 Environmental sensor
15 Environmental information acquirer
16 Biometric sensor
17 Biometric information acquirer
20 Storage
21 Information writer
30 Internal bus
31 Processor
32 Main storage
33 External storage
34 Operation device
35 Display
36 Voice inputter
37 Voice outputter
38 Camera
39 Communication circuit
40 Timer
41 Program
50 User information storage
60 Distance sensor
61 Distance information acquirer
62 Imager
70 Time measurer
80 Estimator
T Source
t Odorant

What is claimed is:
1. An information management system, comprising:
a portable terminal including:
a display device for displaying information;
an input device for receiving input from a user;
an odor sensor to sense an odor, the odor sensor including a plurality of sensitive membranes including acceptors configured to absorb the odor causing physical changes in the sensitive membranes;
an imager to image a source of the odor;
a distance sensor to sense information on a distance between the odor sensor and the source of the odor; and
a processor programmed to function as:
an odor information generator to detect a physical change in the sensitive membranes of the odor sensor and determine a kind of odor based on the detected physical change in the sensitive membranes;
a time measurer to generate information on a date and time when the odor is sensed by the odor sensor;
a user information acquirer to acquire user information indicating an attribute of the user by displaying an input image on the display device prompting the user to input information associated with the user upon receiving an odor detection signal from the odor sensor indicating a sensed odor based on a change in a physical property of a corresponding sensitive membrane;
a preference information inputter into which preference information indicating a preference of the user for the odor sensed by the odor sensor is input via the input device;
an environmental information acquirer to acquire environmental information on space in which the odor drifts;
a biometric information acquirer to sense biometric information on the user;
a storage that associates odor information indicating the kind of the odor determined by the odor information generator, the user information acquired by the user information acquirer, the preference information input into the preference information inputter, the environmental information by the environmental information acquirer, the biometric information by the biometric information acquirer, the image of the source of the odor, the distance between the odor sensor and the source of the odor, and the information on a date and time, with each other, and stores the odor information, the user information, the preference information, the environmental information, the biometric information, the image of the source of the odor, the distance between the odor sensor and the source of the odor, and the information on a date and time; and
an estimator to calculate statistical information relating to a difference in the preference of the user for the odor with reference to the attribute of the user, the environmental information, the biometric information, the odor information, the user information, the preference information, the image of the source of the odor, the distance between the odor sensor and the source of the odor, and the information on the date and time that are stored in the storage;
wherein the estimator estimates, with reference to the information stored in the storage, a preference of a novel user for an odor based on an attribute of the novel user, the environmental information, the biometric information, the odor information, the image of the source of the odor, the distance between the odor sensor and the source of the odor, and the information on the date and time, to display on the display device a result estimated by the estimator.

2. The information management system according to claim 1, wherein the user information includes at least one piece of information of an age, gender, area, body type, living environment, occupation, hobby, and physical condition of the user.

3. The information management system according to claim 1, wherein the odor information includes strength of the odor.

4. The information management system according to claim 1, wherein the environmental information includes at least one piece of information of temperature, humidity, air pressure, weather, and positional information.

5. The information management system according to claim 1, wherein the biometric information includes at least one piece of information of a body temperature, blood pressure, heart rate, electrocardiogram, brain wave, and respiratory sound of the user.

6. The information management system according to claim 1, wherein the distance sensor includes at least one of a camera and a ultrasonic sensor.

7. The information management system according to claim 1, further comprising:
a camera mounted on the portable terminal operating with the imager and the distance sensor.

8. The information management system according to claim 1, wherein the user information acquirer and the preference information inputter are mounted in the portable terminal possessed by the user, and
the storage is mounted in a server computer connected to the portable terminal through a communication network.

9. An information management method, comprising:
sensing, by an odor sensor coupled to a portable terminal, an odor, the odor sensor including a plurality of sensitive membranes including acceptors configured to absorb the odor causing physical changes in the sensitive membranes;
determining, by odor information generator, odor information associated with the sensed odor including a kind of odor based on a detected physical change in the sensitive membranes;
acquiring, by an imager coupled to the portable terminal, image of a source of the odor;
determining, by a distance sensor coupled to the portable terminal, a distance between the odor sensor and the source of the odor based on the image of the source of the odor;
generating, by a time measurer, information on a date and time when the odor is sensed by the odor sensor;
acquiring, by an information processing device, user information indicating an attribute of a user by:
displaying an input image on a display device prompting the user to input information associated with the user upon receiving an odor detection signal from the odor sensor indicating a sensed odor based on a change in a physical property of a corresponding sensitive membrane; and
receiving, from the user via an input device, the user information indicating an attribute of the user;
receiving, by the information processing device via the input device, preference information indicating a preference of the user for the sensed odor;

acquiring, by an environmental information acquirer, environmental information on space in which the odor drifts;
sensing, by a biometric information acquirer, biometric information on the user;
associating, by the information processing device, odor information indicating a kind of the sensed odor, the acquired user information, the input preference information, the environmental information, the biometric information, the image of the source of the odor, the distance between the odor sensor and the source of the odor, and the information on a date and time, with each other, and storing, by the information processing device, the odor information, the user information, the preference information, the environmental information, the biometric information, the image of the source of the odor, the distance between the odor sensor and the source of the odor, and the information on a date and time;
calculating, by an estimator, statistical information relating to a difference in the preference of the user for the odor with reference to the attribute of the user, the environmental information, the biometric information, the odor information, the user information, the preference information, the image of the source of the odor, the distance between the odor sensor and the source of the odor, and the information on the date and time that are stored in the storage;
estimating, by the estimator, with reference to the information stored in the storage, a preference of a novel user for an odor based on an attribute of the novel user, the environmental information, the biometric information, the odor information, the image of the source of the odor, the distance between the odor sensor and the source of the odor, and the information on the date and time; and
displaying the statistical information on a display device indicating the estimate of the preference of the novel user for the odor.

10. A non-transitory computer-readable storage medium storing a program causing a computer to function as:
a portable terminal including:
a display device for displaying information;
an input device for receiving input from a user;
an odor sensor to sense an odor, the odor sensor including a plurality of sensitive membranes including acceptors configured to absorb the odor causing physical changes in the sensitive membranes;
an imager to image the source of the odor; and
a distance sensor to sense information on a distance between the odor sensor and the source of the odor;
an odor information generator to detect a physical change in the sensitive membranes of the odor sensor and determine a kind of odor based on the detected physical change in the sensitive membranes;
a time measurer to generate information on a date and time when the odor is sensed by the odor sensor;
a user information acquirer to acquire user information indicating an attribute of the user by displaying an input image on the display device prompting the user to input information associated with the user upon receiving an odor detection signal from the odor sensor indicating a sensed odor based on a change in a physical property of a corresponding sensitive membrane;

a preference information inputter to input preference information indicating a preference of the user for an odor sensed by an odor sensor to sense the odor via the input device;
an environmental information acquirer to acquire environmental information on space in which the odor drifts;
a biometric information acquirer to sense biometric information on the user;
a storage to associate odor information indicating the kind of the odor determined by the odor information generator, the user information acquired by the user information acquirer, the preference information input into the preference information inputter, the environmental information by the environmental information acquirer, the biometric information by the biometric information acquirer, the image of the source of the odor, the distance between the odor sensor and the source of the odor, and the information on a date and time, with each other, and to store the odor information, the user information, the preference information, the environmental information, the biometric information, the image of the source of the odor, the distance between the odor sensor and the source of the odor, and the information on a date and time; and
an estimator to calculate statistical information relating to a difference in the preference of the user for the odor with reference to the attribute of the user, the environmental information, the biometric information, the odor information, the user information, the preference information, the image of the source of the odor, the distance between the odor sensor and the source of the odor, and the information on the date and time that are stored in the storage;
wherein the estimator estimates, with reference to the information stored in the storage, a preference of a novel user for an odor based on an attribute of the novel user, the environmental information, the biometric information, the odor information, the image of the source of the odor, the distance between the odor sensor and the source of the odor, and the information on the date and time, to display on the display device a result estimated by the estimator.

* * * * *